(12) United States Patent
Liu et al.

(10) Patent No.: US 9,572,522 B2
(45) Date of Patent: Feb. 21, 2017

(54) TEAR FLUID CONDUCTIVITY SENSOR

(71) Applicant: Verily Life Sciences LLC, Mountain View, CA (US)

(72) Inventors: Zenghe Liu, Alameda, CA (US); Huanfen Yao, Sunnyvale, CA (US)

(73) Assignee: Verily Life Sciences LLC, Mountain View, CA (US)

( * ) Notice: Subject to any disclaimer, the term of this patent is extended or adjusted under 35 U.S.C. 154(b) by 503 days.

(21) Appl. No.: 14/136,895

(22) Filed: Dec. 20, 2013

(65) Prior Publication Data

US 2015/0173658 A1    Jun. 25, 2015

(51) Int. Cl.
| | |
|---|---|
| *A61B 5/00* | (2006.01) |
| *A61B 5/145* | (2006.01) |
| *A61B 5/053* | (2006.01) |
| *A61B 5/1468* | (2006.01) |

(52) U.S. Cl.
CPC ......... *A61B 5/14507* (2013.01); *A61B 5/0031* (2013.01); *A61B 5/053* (2013.01); *A61B 5/1468* (2013.01); *A61B 5/6821* (2013.01); *A61B 2560/0219* (2013.01); *A61B 2562/028* (2013.01); *A61B 2562/12* (2013.01)

(58) Field of Classification Search
CPC ... A61B 5/14507; A61B 5/0031; A61B 5/053; A61B 5/1468; A61B 5/6821; A61B 2560/0219; A61B 2562/028; A61B 2562/12
See application file for complete search history.

(56) References Cited

U.S. PATENT DOCUMENTS

| | | | |
|---|---|---|---|
| 3,958,560 | A | 5/1976 | March |
| 4,014,321 | A | 3/1977 | March |
| 4,055,378 | A | 10/1977 | Feneberg et al. |
| 4,122,942 | A | 10/1978 | Wolfson |

(Continued)

FOREIGN PATENT DOCUMENTS

| | | |
|---|---|---|
| EP | 0369942 | 5/1990 |
| EP | 0686372 | 12/1995 |

(Continued)

OTHER PUBLICATIONS

Radiometer Analytical SAS, "Conductivity Theory and Practice," 2004 (50 pages).

(Continued)

*Primary Examiner* — Navin Natnithithadha
*Assistant Examiner* — Eric Messersmith
(74) *Attorney, Agent, or Firm* — McDonnell Boehnen Hulbert & Berghoff LLP

(57) ABSTRACT

Disclosed herein is a fluid conductivity sensor that can be used to obtain in-vivo measurements of conductivity of biological fluid samples, for example, to determine osmolarity. The conductivity sensor can be disposed on a substrate that is at least partially embedded within a polymeric material of a body-mountable device. The conductivity sensor can include a frame having a trench formed therein that defines a fluid sample cell. First and second electrodes can be formed on sidewalls of the trench, such that the first and second electrodes are on opposite sides of the fluid sample cell. A controller in the body-mountable device can operate the sensor by applying a voltage to the electrodes and measuring a current through a fluid occupying the fluid sample cell. The body-mountable device may indicate the current measurements wirelessly using an antenna.

14 Claims, 14 Drawing Sheets

(56) References Cited

U.S. PATENT DOCUMENTS

| | | |
|---|---|---|
| 4,136,250 A | 1/1979 | Mueller et al. |
| 4,143,949 A | 3/1979 | Chen |
| 4,153,641 A | 5/1979 | Deichert et al. |
| 4,214,014 A | 7/1980 | Hofer et al. |
| 4,309,085 A | 1/1982 | Morrison |
| 4,312,575 A | 1/1982 | Peyman et al. |
| 4,401,371 A | 8/1983 | Neefe |
| 4,463,149 A | 7/1984 | Ellis |
| 4,555,372 A | 11/1985 | Kunzler et al. |
| 4,604,479 A | 8/1986 | Ellis |
| 4,632,844 A | 12/1986 | Yanagihara et al. |
| 4,686,267 A | 8/1987 | Ellis et al. |
| 4,740,533 A | 4/1988 | Su et al. |
| 4,826,936 A | 5/1989 | Ellis |
| 4,996,275 A | 2/1991 | Ellis et al. |
| 4,997,770 A | 3/1991 | Giles et al. |
| 5,032,658 A | 7/1991 | Baron et al. |
| 5,034,461 A | 7/1991 | Lai et al. |
| 5,070,215 A | 12/1991 | Bambury et al. |
| 5,135,297 A | 8/1992 | Valint et al. |
| 5,143,080 A | 9/1992 | York |
| 5,177,165 A | 1/1993 | Valint et al. |
| 5,177,168 A | 1/1993 | Baron et al. |
| 5,219,965 A | 6/1993 | Valint et al. |
| 5,260,000 A | 11/1993 | Nandu et al. |
| 5,271,875 A | 12/1993 | Appleton et al. |
| 5,310,779 A | 5/1994 | Lai |
| 5,321,108 A | 6/1994 | Kunzler et al. |
| 5,326,584 A | 7/1994 | Kamel et al. |
| 5,336,797 A | 8/1994 | McGee et al. |
| 5,346,976 A | 9/1994 | Ellis et al. |
| 5,358,995 A | 10/1994 | Lai et al. |
| 5,364,918 A | 11/1994 | Valint et al. |
| 5,387,662 A | 2/1995 | Kunzler et al. |
| 5,449,729 A | 9/1995 | Lai |
| 5,472,436 A | 12/1995 | Fremstad |
| 5,512,205 A | 4/1996 | Lai |
| 5,585,871 A | 12/1996 | Linden |
| 5,610,252 A | 3/1997 | Bambury et al. |
| 5,616,757 A | 4/1997 | Bambury et al. |
| 5,682,210 A | 10/1997 | Weirich |
| 5,708,094 A | 1/1998 | Lai et al. |
| 5,710,302 A | 1/1998 | Kunzler et al. |
| 5,714,557 A | 2/1998 | Kunzler et al. |
| 5,726,733 A | 3/1998 | Lai et al. |
| 5,760,100 A | 6/1998 | Nicholson et al. |
| 5,908,906 A | 6/1999 | Kunzler et al. |
| 5,981,669 A | 11/1999 | Valint et al. |
| 6,087,941 A | 7/2000 | Ferraz et al. |
| 6,131,580 A | 10/2000 | Ratner et al. |
| 6,193,369 B1 | 2/2001 | Valint et al. |
| 6,200,626 B1 | 3/2001 | Grobe et al. |
| 6,213,604 B1 | 4/2001 | Valint et al. |
| 6,312,393 B1 | 11/2001 | Abreu |
| 6,348,507 B1 | 2/2002 | Heiler et al. |
| 6,366,794 B1 | 4/2002 | Moussy et al. |
| 6,423,001 B1 | 7/2002 | Abreu |
| 6,428,839 B1 | 8/2002 | Kunzler et al. |
| 6,431,705 B1 | 8/2002 | Linden |
| 6,440,571 B1 | 8/2002 | Valint et al. |
| 6,450,642 B1 | 9/2002 | Jethmalani et al. |
| 6,532,298 B1 | 3/2003 | Cambier et al. |
| 6,550,915 B1 | 4/2003 | Grobe, III |
| 6,570,386 B2 | 5/2003 | Goldstein |
| 6,579,235 B1 | 6/2003 | Abita et al. |
| 6,599,559 B1 | 7/2003 | McGee et al. |
| 6,614,408 B1 | 9/2003 | Mann |
| 6,630,243 B2 | 10/2003 | Valint et al. |
| 6,638,563 B2 | 10/2003 | McGee et al. |
| 6,726,322 B2 | 4/2004 | Andino et al. |
| 6,735,328 B1 | 5/2004 | Helbing et al. |
| 6,779,888 B2 | 8/2004 | Marmo |
| 6,804,560 B2 | 10/2004 | Nisch et al. |
| 6,851,805 B2 | 2/2005 | Blum et al. |
| 6,885,818 B2 | 4/2005 | Goldstein |
| 6,939,299 B1 | 9/2005 | Petersen et al. |
| 6,980,842 B2 | 12/2005 | March et al. |
| 7,018,040 B2 | 3/2006 | Blum et al. |
| 7,129,717 B2 | 10/2006 | Donsky |
| 7,131,945 B2 | 11/2006 | Fink et al. |
| 7,169,106 B2 | 1/2007 | Fleischman et al. |
| 7,398,119 B2 | 7/2008 | Lambert et al. |
| 7,423,801 B2 | 9/2008 | Kaufman et al. |
| 7,429,465 B2 | 9/2008 | Muller et al. |
| 7,441,892 B2 | 10/2008 | Hsu |
| 7,443,016 B2 | 10/2008 | Tsai et al. |
| 7,450,981 B2 | 11/2008 | Jeon |
| 7,639,845 B2 | 12/2009 | Utsunomiya |
| 7,654,671 B2 | 2/2010 | Glynn |
| 7,699,465 B2 | 4/2010 | Dootjes et al. |
| 7,728,949 B2 | 6/2010 | Clarke et al. |
| 7,751,896 B2 | 7/2010 | Graf et al. |
| 7,799,243 B2 | 9/2010 | Mather et al. |
| 7,809,417 B2 | 10/2010 | Abreu |
| 7,878,650 B2 | 2/2011 | Fritsch et al. |
| 7,885,698 B2 | 2/2011 | Feldman |
| 7,907,931 B2 | 3/2011 | Hartigan et al. |
| 7,926,940 B2 | 4/2011 | Blum et al. |
| 7,931,832 B2 | 4/2011 | Pugh et al. |
| 7,964,390 B2 | 6/2011 | Rozakis et al. |
| 7,987,702 B2 | 8/2011 | Sullivan |
| 8,080,187 B2 | 12/2011 | Tepedino, Jr. et al. |
| 8,096,654 B2 | 1/2012 | Amirparviz et al. |
| 8,118,752 B2 | 2/2012 | Hetling et al. |
| 8,142,016 B2 | 3/2012 | Legerton et al. |
| 8,224,415 B2 | 7/2012 | Budiman |
| 2002/0193674 A1 | 12/2002 | Fleischman et al. |
| 2003/0179094 A1 | 9/2003 | Abreu |
| 2004/0027536 A1 | 2/2004 | Blum et al. |
| 2004/0116794 A1 | 6/2004 | Fink et al. |
| 2005/0045589 A1 | 3/2005 | Rastogi et al. |
| 2005/0221276 A1 | 10/2005 | Rozakis et al. |
| 2007/0016074 A1 | 1/2007 | Abreu |
| 2007/0030443 A1 | 2/2007 | Chapoy et al. |
| 2007/0121065 A1 | 5/2007 | Cox et al. |
| 2007/0188710 A1 | 8/2007 | Hetling et al. |
| 2008/0208335 A1 | 8/2008 | Blum et al. |
| 2008/0218696 A1 | 9/2008 | Mir |
| 2009/0033863 A1 | 2/2009 | Blum et al. |
| 2009/0036761 A1 | 2/2009 | Abreu |
| 2009/0057164 A1 | 3/2009 | Minick et al. |
| 2009/0076367 A1 | 3/2009 | Sit et al. |
| 2009/0118604 A1 | 5/2009 | Phan et al. |
| 2009/0189830 A1 | 7/2009 | Deering et al. |
| 2009/0196460 A1 | 8/2009 | Jakobs et al. |
| 2010/0001926 A1 | 1/2010 | Amirparviz et al. |
| 2010/0013114 A1 | 1/2010 | Bowers et al. |
| 2010/0016704 A1 | 1/2010 | Naber et al. |
| 2010/0028559 A1 | 2/2010 | Yan et al. |
| 2010/0072643 A1 | 3/2010 | Pugh et al. |
| 2010/0109175 A1 | 5/2010 | Pugh et al. |
| 2010/0110372 A1 | 5/2010 | Pugh et al. |
| 2010/0113901 A1 | 5/2010 | Zhang et al. |
| 2010/0133510 A1 | 6/2010 | Kim et al. |
| 2010/0249548 A1 | 9/2010 | Muller |
| 2011/0015512 A1 | 1/2011 | Pan et al. |
| 2011/0028807 A1 | 2/2011 | Abreu |
| 2011/0040161 A1 | 2/2011 | Abreu |
| 2011/0055317 A1 | 3/2011 | Vonog et al. |
| 2011/0063568 A1 | 3/2011 | Meng et al. |
| 2011/0084834 A1 | 4/2011 | Sabeta |
| 2011/0116035 A1 | 5/2011 | Fritsch et al. |
| 2011/0157541 A1 | 6/2011 | Peyman |
| 2011/0157544 A1 | 6/2011 | Pugh et al. |
| 2011/0184271 A1 | 7/2011 | Veciana et al. |
| 2011/0274680 A1 | 11/2011 | Mazed et al. |
| 2011/0286064 A1 | 11/2011 | Burles et al. |
| 2011/0298794 A1 | 12/2011 | Freedman |
| 2012/0026458 A1 | 2/2012 | Qiu et al. |
| 2012/0038881 A1 | 2/2012 | Amirparviz et al. |
| 2012/0041287 A1 | 2/2012 | Goodall et al. |
| 2012/0041552 A1 | 2/2012 | Chuck et al. |
| 2012/0069254 A1 | 3/2012 | Burton |
| 2012/0075168 A1 | 3/2012 | Osterhout et al. |

(56) References Cited

U.S. PATENT DOCUMENTS

| | | |
|---|---|---|
| 2012/0075574 A1 | 3/2012 | Pugh et al. |
| 2012/0078071 A1 | 3/2012 | Bohm et al. |
| 2012/0088258 A1 | 4/2012 | Bishop et al. |
| 2012/0092612 A1 | 4/2012 | Binder et al. |
| 2012/0109296 A1 | 5/2012 | Fan |
| 2012/0177576 A1 | 7/2012 | Hu |
| 2012/0201755 A1 | 8/2012 | Rozakis et al. |
| 2012/0245444 A1 | 9/2012 | Otis et al. |
| 2012/0259188 A1 | 10/2012 | Besling |
| 2013/0194540 A1 | 8/2013 | Pugh et al. |

FOREIGN PATENT DOCUMENTS

| | | |
|---|---|---|
| EP | 1061874 | 12/2000 |
| EP | 1818008 | 8/2007 |
| EP | 1947501 | 7/2008 |
| EP | 1617757 | 8/2009 |
| EP | 2457122 | 5/2012 |
| WO | 95/04609 | 2/1995 |
| WO | 01/16641 | 3/2001 |
| WO | 01/34312 | 5/2001 |
| WO | 03/065876 | 8/2003 |
| WO | 2004/060431 | 7/2004 |
| WO | 2004/064629 | 8/2004 |
| WO | 2006/015315 | 2/2006 |
| WO | 2009/094643 | 7/2009 |
| WO | 2010/105728 | 9/2010 |
| WO | 2010/133317 | 11/2010 |
| WO | 2011/011344 | 1/2011 |
| WO | 2011/034592 | 3/2011 |
| WO | 2011/035228 | 3/2011 |
| WO | 2011/035262 | 3/2011 |
| WO | 2011/083105 | 7/2011 |
| WO | 2011/163080 | 12/2011 |
| WO | 2012/035429 | 3/2012 |
| WO | 2012/037455 | 3/2012 |
| WO | 2012/051167 | 4/2012 |
| WO | 2012/051223 | 4/2012 |
| WO | 2012052765 | 4/2012 |

OTHER PUBLICATIONS

TearLab Osmolarity System, Clinical Utility Guide, 2010 (8 pages).

Badugu et al., "A Glucose Sensing Contact Lens: A Non-Invasive Technique for Continuous Physiological Glucose Monitoring," Journal of Fluorescence, Sep. 2003, pp. 371-374, vol. 13, No. 5.

Carlson et al., "A 20 mV Input Boost Converter With Efficient Digital Control for Thermoelectric Energy Harvesting," IEEE Journal of Solid-State Circuits, Apr. 2010, pp. 741-750, vol. 45, No. 4.

Chu et al., "Biomedical soft contact-lens sensor for in situ ocular biomonitoring of tear contents," Biomed Microdevices, 2011, pp. 603-611, vol. 13.

Chu et al., "Soft contact lens biosensor for in situ monitoring of tear glucose as non-invasive blood sugar assessment," Talanta, 2011, pp. 960-965, vol. 83.

Ho et al., "Contact Lens With Integrated Inorganic Semiconductor Devices," MEMS 2008. IEEE 21st International Conference on. IEEE, 2008., pp. 403-406.

Lahdesmaki et al., "Possibilities for Continuous Glucose Monitoring by a Functional Contact Lens," IEEE Instrumentation & Measurement Magazine, Jun. 2010, pp. 14-17.

Lingley et al., "A contact lens with integrated micro solar cells," Microsyst Technol, 2012, pp. 453-458, vol. 18.

Parviz, Babak A., "For Your Eyes Only," IEEE Spectrum, Sep. 2009, pp. 36-41.

Saeedi, E. et al., "Self-assembled crystalline semiconductor optoelectronics on glass and plastic," J. Micromech. Microeng., 2008, pp. 1-7, vol. 18.

Saeedi et al., "Self-Assembled Inorganic Micro-Display on Plastic," Micro Electro Mechanical Systems, 2007. MEMS. IEEE 20th International Conference on. IEEE, 2007., pp. 755-758.

Sensimed Triggerfish, Sensimed Brochure, 2010, 10 pages.

Shih, Yi-Chun et al., "An Inductorless DC-DC Converter for Energy Harvesting With a 1.2-μW Bandgap-Referenced Output Controller," IEEE Transactions on Circuits and Systems—II: Express Briefs, Dec. 2011, pp. 832-836, vol. 58, No. 12.

Shum et al., "Functional modular contact lens," Proc. of SPIE, 2009, pp. 73970K-1 to 73970K-8, vol. 7397.

Stauth et al., "Self-assembled single-crystal silicon circuits on plastic," PNAS, Sep. 19, 2006, pp. 13922-13927, vol. 103, No. 38.

Yao, H. et al., "A contact lens with integrated telecommunication circuit and sensors for wireless and continuous tear glucose monitoring," J. Micromech. Microeng., 2012, pp. 1-10, vol. 22.

Yao, H. et al., "A Dual Microscal Glucose Sensor on a Contact Lens, Tested in Conditions Mimicking the Eye," Micro Electro Mechanical Systems (MEMS), 2011 IEEE 24th International Conference on. IEEE, 2011, pp. 25-28.

Yao et al., "A contact lens with embedded sensor for monitoring tear glucose level," Biosensors and Bioelectronics, 2011, pp. 3290-3296, vol. 26.

Yao, H. et al., "A Soft Hydrogel Contact Lens with an Encapsulated Sensor for Tear Glucose Monitoring," Micro Electro Mechanical Systems (MEMS), 2012 IEEE 25th International Conference on. IEEE, 2012, pp. 769-772.

Yeager et al., "A 9 μA, Addressable Gent Sensor Tag for Biosignal Acquistion," IEEE Journal of Solid-State Circuits, Oct. 2010, pp. 2198-2209, vol. 45, No. 10.

Zhang et al., "Design for Ultra-Low Power Biopotential Amplifiers for Biosignal Acquistion Applications," IEEE Transactions on Biomedical Circuits and Systems, 2012, pp. 344-355, vol. 6, No. 4.

Bionic contact lens 'to project emails before eyes,' http://www.kurzweilai.netforums/topic/bionic-contact-lens-to-project-emails-before-eyes, Last accessed Mar. 14, 2012, 2 pages.

Brahim, et al., "Polypyrrole-hydrogel composites for the construction of clinically important biosensors," 2002, Biosensors & Bioelectronics, pp. 53-59, vol. 17.

Chen, et al., "Microfabricated Implantable Parylene-Based Wireless Passive Intraocular Pressure Sensors," Journal of Microelectromechanical Systems, Dec. 2008, pp. 1342-1351, vol. 17, No. 6.

Chu, et al., "Soft Contact-lens Sensor for Monitoring Tear Sugar as Novel Wearable Device of Body Sensor Network," http://www.ksi edu/seke/dms11/DMS/2_Kohji_Mitsubayashi.pdf, Last accessed Jul. 27, 2012, 4 pages.

"Contact Lenses: Look Into My Eyes," The Economist, Jun. 2, 2011 , http://www.econonnist.conn/node/18750624/print, Last accessed Mar. 13, 2012, 8 pages.

Haders, "New Controlled Release Technologies Broaden Opportunities for Ophthalmic Therapies," Drug Delivery Technology, Jul./Aug. 2009, pp. 48-53, vol. 8, No. 7.

Holloway, "Microsoft developing electronic contact lens to monitor blood sugar," Gizmag, Jan. 5, 2012, http://www.gizmag.com/microsoft-electronic-diabetic-contact-lens/20987/, Last accessed Mar. 13, 2012. 5 pages.

Huang, et al., "Wrinkling of Ultrathin Polymer Films," Mater. Res. Soc. Symp. Proc., 2006, 6 pages, vol. 924, Materials Research Society.

Hurst, "How contact lenses could help save your life," Mail Online, Apr. 19, 2010, http://www.dailymail.co.uk/health/article-1267345/How-contact-lenses-help-save-life.html, Last accessed Jul. 27, 2012.

Liao, et al., "A 3-μW CMOS Glucose Sensor for Wireless Contact-Lens Tear Glucose Monitoring ," IEEE Journal of Solid-State Circuits, Jan. 2012, pp. 335-344, vol. 47, No. 1.

Liao, et al., "A 3-μW Wirelessly Powered CMOS Glucose Sensor for an Active Contact Lens," 2011 IEEE International Solid-State Circuits Conference, Session 2, Feb. 21, 2011, 3 pages.

Lingley, et al., "A Single-Pixel Wireless Contact Lens Display," Journal of Micromechanics and Microengineering, 2011, pp. 1-8.

Lingley, et al., "Multipurpose integrated active contact lenses," SPIE, 2009, 2 pages.

Liu, et al., "Miniature Amperometric Self-Powered Continuous Glucose Sensor with Linear Response," Analytical Chemistry, 2012, 7 pages.

(56) References Cited

OTHER PUBLICATIONS

Loncar, et al., "Design and Fabrication of Silicon Photonic Crystal Optical Waveguides," Journal of Lightwave Technology, Oct. 2000, pp. 1402-1411, vol. 18, No. 10.
Murdan, "Electro-responsive drug delivery from hydrogels," Journal of Controlled Release, 2003, pp. 1-17, vol. 92.
Pandey, et al., "A Fully Integrated RF-Powered Contact Lens With a Single Element Display," IEEE Transactions on Biomedical Circuits and Systems, Dec. 2010, pp. 454-461, vol. 4, No. 6.
Parviz, Babak A., "Augmented Reality in a Contact Lens," IEEE Spectrum, Sep. 2009, http://spectrum.ieee.org/biomedical/bionics/augmented-reality-in-a-contact-lens/0, Last accessed Mar. 14, 2012, 6 pages.
Selner, et al., "Novel Contact Lens Electrode Array for Multi-electrode Electroretinography (meERG)," IEEE, 2011, 2 pages.
Singh, et al., "Novel Approaches in Formulation and Drug Delivery using Contact Lenses," Journal of Basic and Clinical Pharmacy, May 2011, pp. 87-101, vol. 2, Issue 2.
Thomas, et al., "Functional Contact Lenses for Remote Health Monitoring in Developing Countries," IEEE Global Humanitarian Technology Conference, 2011, pp. 212-217, IEEE Computer Society.
Tweedie, et al., "Contact creep compliance of viscoelastic materials via nanoindentation," J. Mater. Res., Jun. 2006, pp. 1576-1589, vol. 21, No. 2, Materials Research Society.
Wall, K., "Active contact lens that lets you see like the Terminator patented," Feb. 10, 2012, http://vvww.patexia.com/feed/active-contact-lens-that-lets-you-see-like-the-terminator-patented-2407, Last accessed Mar. 28, 2012, 5 pages.
Zarbin, et al., "Nanotechnology in ophthalmology," Can J Ophthalmol, 2010, pp. 457-476, vol. 45, No. 5.
International Searching Authority, International Search Report and Written Opinion for Application No. PCT/US2014/066323 mailed Feb. 17, 2015, 10 pages.

TEAR FLUID CONDUCTIVITY SENSOR

BACKGROUND

Unless otherwise indicated herein, the materials described in this section are not prior art to the claims in this application and are not admitted to be prior art by inclusion in this section.

The eye is coated by a layer of tear film secreted by the lacrimal gland and distributed over the eye by motion of the eyelids. The tear film layer serves a number of biological functions including to lubricate and protect the corneal surface (epithelium). Dry eye disease, or ocular surface dryness is characterized by irritation of the epithelium and associated discomfort. The condition can be due in part to low aqueous tear flow and/or excess tear fluid evaporation, which results in tear fluid with a relatively elevated solute concentration (i.e., hyperosmolarity). Hyperosmolarity may also be due in part to irregularities in various physiological osmo-regulation and compensatory mechanisms responsible for tear fluid homeostasis. In any event, the increased concentration of solutes in the tear fluid causes irritation of the epithelium, which then leads to compensatory reactions in the eye (e.g., immunological inflammation) due to the epithelial damage.

SUMMARY

An osmolarity sensor can includes a nanoliter-scale fluid sample cell to obtain a conductivity measurement from a small sample volume. The conductivity sensor can have a frame in which a trench is formed, such that the trench defines a sample volume of the sensor. The conductivity sensor can further include electrodes disposed on opposing sidewalls of the trench such that the electrodes are positioned facing one another from opposing sides of the sample volume. In an example, the conductivity sensor may be included in an eye-mountable device similar to a contact lens that can be equipped with embedded electronics for providing power, communication, and various logic functions. An osmolarity sensor can be included in the contact lens and the electronics can operate the sensor to obtain readings and communicate the results. A channel in the eye-mountable device may expose the sensor to tear fluid, and the conductivity of the tear fluid can then be measured, which provides an indication of osmolarity.

Some embodiments of the present disclosure provide a device. The device can include a polymeric material, a substrate at least partially embedded within the polymeric material, an antenna disposed on the substrate, a conductivity sensor, and a controller. The conductivity sensor can be disposed on the substrate. The conductivity sensor can include a frame, a first electrode, and a second electrode. The frame can have a trench formed therein that defines a fluid sample cell. The trench can include a first sidewall and a second sidewall. The first electrode can be formed on the first sidewall. The second electrode can be formed on the second sidewall such that the first and second electrodes are on opposite sides of the fluid sample cell. The controller can be electrically connected to the sensor electrodes and the antenna. The controller can be configured to: (i) apply a voltage to the electrodes sufficient to generate a current through the electrodes related to a conductance of a fluid occupying the fluid sample cell; (ii) measure the generated current; and (iii) use the antenna to indicate the measured current.

Some embodiments of the present disclosure provide a method. The method can include forming, in a substrate, a trench having a first sidewall and a second sidewall. The method can include patterning a selectively etchable material on the sidewalls of the trench. The method can include etching a bottom of the trench with an isotropic etchant so as to create a cavity in the substrate originating from the bottom of the trench. The cavity can extend beyond a width of the trench defined by a separation distance between the sidewalls. The method can include forming a conductive layer over the trench such that the conductive layer includes a first electrode on the first sidewall and a second electrode on the second sidewall, wherein the first and second electrodes are separated from one another by the cavity.

Some embodiments of the present disclosure provide a method. The method can include applying a voltage to a first electrode and a second electrode of a conductivity sensor sufficient to generate a current through the electrodes related to a conductance of a tear fluid occupying a fluid sample cell between the first and second electrodes. The conductivity sensor can be disposed on a substrate embedded in an eye-mountable device. The conductivity sensor can include a frame having a trench formed therein that defines the fluid sample cell. The trench can include a first sidewall and a second sidewall. The first electrode can be formed on the first sidewall, and the second electrode can be formed on the second sidewall such that the first and second electrodes are on opposite sides of the fluid sample cell. The method can include measuring the generated current. The method can include using an antenna disposed on the substrate of the eye-mountable device to indicate the measured current.

Some embodiments of the present disclosure include means for obtaining an in-vivo tear film conductivity measurement. Some embodiments of the present disclosure include means for applying a voltage to a first electrode and a second electrode of a conductivity sensor sufficient to generate a current through the electrodes related to a conductance of a tear fluid occupying a fluid sample cell between the first and second electrodes. The conductivity sensor can be disposed on a substrate embedded in an eye-mountable device. The conductivity sensor can include a frame having a trench formed therein that defines the fluid sample cell. The trench can include a first sidewall and a second sidewall. The first electrode can be formed on the first sidewall, and the second electrode can be formed on the second sidewall such that the first electrode faces the second electrode from opposite sides of the fluid sample cell. Some embodiments of the present disclosure include means for measuring the generated current. Some embodiments of the present disclosure include means for using an antenna disposed on the substrate of the eye-mountable device to indicate the measured current.

These as well as other aspects, advantages, and alternatives, will become apparent to those of ordinary skill in the art by reading the following detailed description, with reference where appropriate to the accompanying drawings.

DETAILED DESCRIPTION

Figure 1:
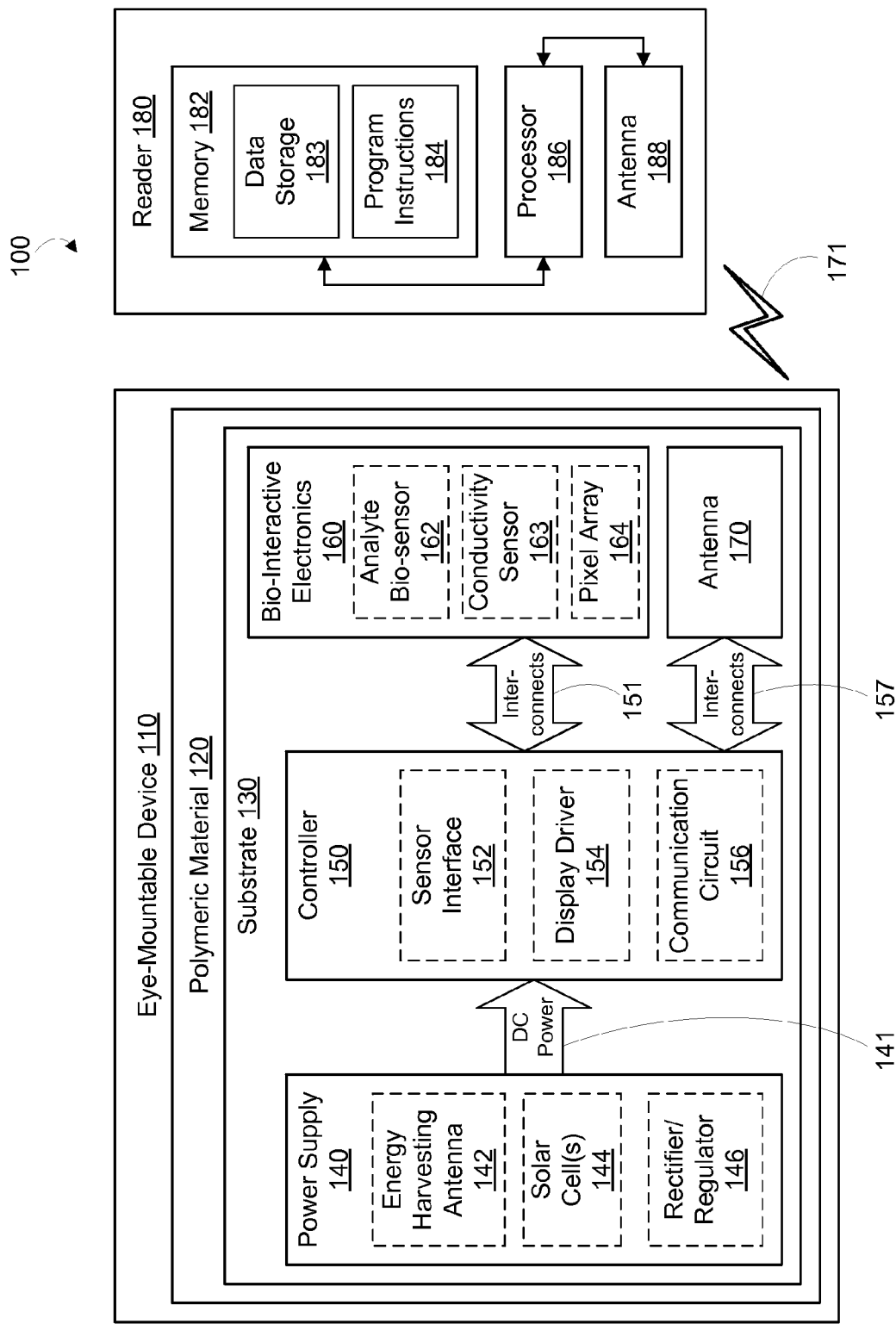
FIG. 1 is a block diagram of an example system that includes an eye-mountable device in wireless communication with an external reader.

In the following detailed description, reference is made to the accompanying figures, which form a part hereof. In the figures, similar symbols typically identify similar components, unless context dictates otherwise. The illustrative embodiments described in the detailed description, figures, and claims are not meant to be limiting. Other embodiments may be utilized, and other changes may be made, without departing from the scope of the subject matter presented herein. It will be readily understood that the aspects of the present disclosure, as generally described herein, and illustrated in the figures, can be arranged, substituted, combined, separated, and designed in a wide variety of different configurations, all of which are explicitly contemplated herein.

I. Overview

An osmolarity sensor is disclosed that includes a nanoliter-scale fluid sample cell useful in obtaining a conductivity measurement from a small sample volume. A method of fabricating such an osmolarity sensor is also disclosed herein. In an example application, the sensor may be embedded in a body-mountable or implantable device formed of a polymeric material and then used to obtain osmolarity measurements in-vivo. For instance, an eye-mountable device similar to a contact lens can be equipped with embedded electronics for providing power, communication, and various logic functions. An osmolarity sensor can be included in the contact lens and the electronics can operate the sensor to obtain readings and communicate the results. A channel in the eye-mountable device may expose the sensor to tear fluid, and the conductivity of the tear fluid can then be measured, which provides an indication of osmolarity.

The contact lens can be formed of a polymeric material shaped to facilitate contact mounting over an eye. A substrate can be embedded within the polymeric material, and electronics can be mounted on the substrate. For example, the substrate may include electronics configured to measure properties of the tear fluid and use an antenna to communicate the results to an external reader. The contact lens can also include an energy harvesting system (e.g., a photovoltaic cell or a radio frequency energy-harvesting antenna) to power the electronics performing the measurement and communication functions. In some examples a chip connects to both the antenna and the sensor, all of which may be disposed on a substrate embedded in the polymeric material of the eye-mountable device. The chip can be configured to: (i) regulate harvested energy from the loop antenna or photovoltaic cell to provide a DC voltage that powers the chip, (ii) operate the sensor to obtain a measurement, and (iii) communicate the results using the antenna.

Dry eye disease can therefore be diagnosed and/or monitored by measuring properties of the tear fluid using a suitable sensor included in the eye-mountable electronics platform described above. Because the conductivity depends on the concentration of electrolytes (e.g., salts), tear fluid conductivity is a good indicator of solute concentration, and therefore a useful indicator of dry eye conditions. A conductivity sensor for an eye-mountable platform may include two or more electrodes that are exposed to the tear fluid while the contact lens is mounted over the eye. The electrodes can be arranged to form opposite sides of a sample volume. The conductivity of the tear fluid can be determined by applying voltage to the electrodes and measuring the resulting current. The results can then be communicated using the antenna, and the sensor system can thereby obtain in-vivo measurements and communicate the results in real time.

For a given conductivity measurement, the current generated in response to a given voltage can depend on the geometry of the electrodes and the volume of the fluid sample situated between the electrodes. Conductivity measurements can be obtained using electrodes that are situated such that the separation distance between the two is substantially constant across the electrodes. Otherwise, the conductivity measurement may be dominated by portions of the fluid sample between the closest areas of the electrodes. In addition, the electrodes may be mounted to a rigid housing or frame to preserve the electrode geometry over time and allow measurements taken at different times to be compared with one another.

In some embodiments, the fluid conductivity can be measured by applying an AC voltage to the electrodes and measuring the resulting current across the electrodes. An AC voltage may be used, instead of a DC voltage, in order to inhibit electrolysis in the fluid and also to prevent accumulation of charge carriers at the two electrodes. In addition, the disclosed sensor can include a tear fluid sample volume with a depth several times greater than a thickness of the tear film coating the eye. As a result, the electric field between the electrodes is not significantly influenced by variations in tear film thickness.

The electrodes can be formed of platinum, palladium, carbon, silver, gold, other suitable conductive materials, and/or combinations of these. The frame can be formed of a silicon wafer with a trench formed therein by patterning a photoresist and etching the trench. The electrodes can then be patterned on opposite sides of the trench (e.g., via deposition). The silicon wafer thereby provides a structural frame that fixes the geometry of the two electrodes.

A body-mountable device may further include an AC voltage generator, a current sensor, and an antenna. The AC voltage generator may apply an AC voltage to the electrodes. The current sensor may measure the resulting current through the electrodes. The antenna may be used to indicate the measured current to an external reader using the antenna. The external reader (or another device) may then use the current measurement to determine the fluid conductivity and/or other characteristics of the fluid.

II. Example Ophthalmic Electronics Platform

FIG. 1 is a block diagram of a system 100 that includes an eye-mountable device 110 in wireless communication with an external reader 180. The exposed regions of the eye-mountable device 110 are made of a polymeric material 120 formed to be contact-mounted to a corneal surface of an eye. A substrate 130 is embedded in the polymeric material 120 to provide a mounting surface for a power supply 140, a controller 150, bio-interactive electronics 160, and a communication antenna 170. The bio-interactive electronics 160 are operated by the controller 150. The power supply 140 supplies operating voltages to the controller 150 and/or the bio-interactive electronics 160. The antenna 170 is operated by the controller 150 to communicate information to and/or from the eye-mountable device 110. The antenna 170, the controller 150, the power supply 140, and the bio-interactive electronics 160 can all be situated on the embedded substrate 130. Because the eye-mountable device 110 includes electronics and is configured to be contact-mounted to an eye, it is also referred to herein as an ophthalmic electronics platform.

To facilitate contact-mounting, the polymeric material 120 can have a concave surface configured to adhere ("mount") to a moistened corneal surface (e.g., by capillary forces with a tear film coating the corneal surface). Additionally or alternatively, the eye-mountable device 110 can be adhered by a vacuum force between the corneal surface and the polymeric material due to the concave curvature. While mounted with the concave surface against the eye, the outward-facing surface of the polymeric material 120 can have a convex curvature that is formed to not interfere with eye-lid motion while the eye-mountable device 110 is mounted to the eye. For example, the polymeric material 120 can be a substantially transparent curved polymeric disk shaped similarly to a contact lens.

The polymeric material 120 can include one or more biocompatible materials, such as those employed for use in contact lenses or other ophthalmic applications involving direct contact with the corneal surface. The polymeric material 120 can optionally be formed in part from such biocompatible materials or can include an outer coating with such biocompatible materials. The polymeric material 120 can include materials configured to moisturize the corneal surface, such as hydrogels and the like. In some embodiments, the polymeric material 120 can be a deformable ("non-rigid") material to enhance wearer comfort. In some embodiments, the polymeric material 120 can be shaped to provide a predetermined, vision-correcting optical power (e.g., for vision correction applications).

The substrate 130 includes one or more surfaces suitable for mounting the bio-interactive electronics 160, the controller 150, the power supply 140, and the antenna 170. The substrate 130 can be employed both as a mounting platform for chip-based circuitry (e.g., by flip-chip mounting to connection pads) and/or as a platform for patterning conductive materials (e.g., gold, platinum, palladium, titanium, copper, aluminum, silver, metals, other conductive materials, combinations of these, etc.) to create electrodes, interconnects, connection pads, antennae, etc. In some embodiments, substantially transparent conductive materials (e.g., indium tin oxide) can be patterned on the substrate 130 to form circuitry, electrodes, etc. For example, the antenna 170 can be formed by forming a pattern of gold or another conductive material on the substrate 130 by deposition, photolithography, electroplating, etc. Similarly, interconnects 151, 157 between the controller 150 and the bio-interactive electronics 160, and between the controller 150 and the antenna 170, respectively, can be formed by depositing suitable patterns of conductive materials on the substrate 130. A combination of microfabrication techniques including, without limitation, the use of photoresists, masks, deposition techniques, and/or plating techniques can be employed to pattern materials on the substrate 130.

The substrate 130 can be a relatively rigid material, such as polyethylene terephthalate ("PET") or another material configured to structurally support the circuitry and/or chip-based electronics within the polymeric material 120. The eye-mountable device 110 can alternatively be arranged with a group of unconnected substrates rather than a single substrate. For example, the controller 150 and a sensor included in the bio-interactive electronics 160 can be mounted to one substrate, while the antenna 170 is mounted to another substrate and the two can be electrically connected via the interconnects 157. In another example, the substrate 130 can include separate partitions that each support separated, overlapped coiled portions of the antenna 170. Such as, for example, an example in which the antenna 170 is divided into multiple windings that wrap around the eye-mountable device 110 circumferentially at respective radii, and are connected in parallel and/or in series. To facilitate movement of the individual windings with respect to one another, and thereby enhance flexibility of the eye-mountable device 110, and help prevent binding, etc., the individual windings may each be mounted on divided portions of the substrate 130, which may substantially correspond to the windings of such an antenna.

In some embodiments, the bio-interactive electronics 160 (and the substrate 130) can be positioned away from the center of the eye-mountable device 110 and thereby avoid interference with light transmission to the central, light-sensitive region of the eye. For example, where the eye-mountable device 110 is shaped as a concave-curved disk, the substrate 130 can be embedded around the periphery (e.g., near the outer circumference) of the disk. In some embodiments, however, the bio-interactive electronics 160 (and the substrate 130) can be positioned in or near the central region of the eye-mountable device 110. Additionally or alternatively, the bio-interactive electronics 160 and/or substrate 130 can be substantially transparent to incoming visible light to mitigate interference with light transmission to the eye. Moreover, in some embodiments, the bio-interactive electronics 160 can include a pixel array 164 that emits and/or transmits light to be received by the eye according to display instructions. Thus, the bio-interactive electronics 160 can optionally be positioned in the center of the eye-mountable device so as to generate perceivable visual cues to a wearer of the eye-mountable device 110, such as by displaying information (e.g., characters, symbols, flashing patterns, etc.) on the pixel array 164.

The substrate 130 can be shaped as a flattened ring with a radial width dimension sufficient to provide a mounting platform for the embedded electronics components. The substrate 130 can have a thickness sufficiently small to allow the substrate 130 to be embedded in the polymeric material 120 without influencing the profile of the eye-mountable device 110. The substrate 130 can have a thickness sufficiently large to provide structural stability suitable for supporting the electronics mounted thereon. For example, the substrate 130 can be shaped as a ring with a diameter of about 10 millimeters, a radial width of about 1 millimeter (e.g., an outer radius 1 millimeter larger than an inner radius), and a thickness of about 50 micrometers. The substrate 130 can optionally be aligned with the curvature of the eye-mounting surface of the eye-mountable device 110 (e.g., convex surface). For example, the substrate 130 can be shaped along the surface of an imaginary cone between two circular segments that define an inner radius and an outer radius. In such an example, the surface of the substrate 130 along the surface of the imaginary cone defines an inclined surface that is approximately aligned with the curvature of the eye mounting surface at that radius.

The power supply 140 is configured to harvest ambient energy to power the controller 150 and bio-interactive electronics 160. For example, a radio-frequency energy-harvesting antenna 142 can capture energy from incident radio radiation. Additionally or alternatively, solar cell(s) 144 ("photovoltaic cells") can capture energy from incoming ultraviolet, visible, and/or infrared radiation. Furthermore, an inertial power scavenging system can be included to capture energy from ambient vibrations. The energy harvesting antenna 142 can optionally be a dual-purpose antenna that is also used to communicate information to the external reader 180. That is, the functions of the communication antenna 170 and the energy harvesting antenna 142 can be accomplished with the same physical antenna.

A rectifier/regulator 146 can be used to condition the captured energy to a stable DC supply voltage 141 that is supplied to the controller 150. For example, the energy harvesting antenna 142 can receive incident radio frequency radiation. Varying electrical signals on the leads of the antenna 142 are output to the rectifier/regulator 146. The rectifier/regulator 146 rectifies the varying electrical signals to a DC voltage and regulates the rectified DC voltage to a level suitable for operating the controller 150. Additionally or alternatively, output voltage from the solar cell(s) 144 can be regulated to a level suitable for operating the controller 150. The rectifier/regulator 146 can include one or more energy storage devices to mitigate high frequency variations in the ambient energy gathering antenna 142 and/or solar cell(s) 144. For example, one or more energy storage devices (e.g., a capacitor, an inductor, etc.) can be connected in parallel across the outputs of the rectifier 146 to regulate the DC supply voltage 141 and configured to function as a low-pass filter.

The controller 150 can be turned on when the DC supply voltage 141 is provided to the controller 150, and the logic in the controller 150 operates the bio-interactive electronics 160 and the antenna 170. The controller 150 can include logic circuitry configured to operate the bio-interactive electronics 160 so as to interact with a biological environment of the eye-mountable device 110. The interaction could involve the use of one or more components, such as an analyte bio-sensor 162, in bio-interactive electronics 160 to obtain input from the biological environment. Additionally or alternatively, the interaction could involve the use of one or more components, such as pixel array 164, to provide an output to the biological environment.

In one example, the controller 150 includes a sensor interface module 152 that is configured to operate analyte bio-sensor 162 and/or the conductivity sensor 163. The analyte bio-sensor 162 can be, for example, an amperometric electrochemical sensor that includes a working electrode and a reference electrode. A voltage can be applied between the working and reference electrodes to cause an analyte to undergo an electrochemical reaction (e.g., a reduction and/or oxidation reaction) at the working electrode. The electrochemical reaction can generate an amperometric current that can be measured through the working electrode. The amperometric current can be dependent on the analyte concentration. Thus, the amount of the amperometric current that is measured through the working electrode can provide an indication of analyte concentration. The conductivity sensor 163 can be, for example, a two-pole sensor in which two electrodes surround a sample volume. Voltage can be applied to the two electrodes (e.g., by the sensor interface 152) and the resulting current through the sample cell can be measured. The current thus provides a measure of the conductivity of the fluid occupying the sample volume. The conductivity can further be used to estimate solute concentration (osmolarity), because the solute concentration of the fluid is generally related to the ion concentration, which is indicated by the conductivity measurement.

The controller 150 can optionally include a display driver module 154 for operating a pixel array 164. The pixel array 164 can be an array of separately programmable light transmitting, light reflecting, and/or light emitting pixels arranged in rows and columns. The individual pixel circuits can optionally include liquid crystal technologies, micro-electromechanical technologies, emissive diode technologies, etc. to selectively transmit, reflect, and/or emit light according to information from the display driver module 154. Such a pixel array 164 can also optionally include more than one color of pixels (e.g., red, green, and blue pixels) to render visual content in color. The display driver module 154 can include, for example, one or more data lines providing programming information to the separately programmed pixels in the pixel array 164 and one or more addressing lines for setting groups of pixels to receive such programming information. Such a pixel array 164 situated on the eye can also include one or more lenses to direct light from the pixel array to a focal plane perceivable by the eye.

The controller 150 can also include a communication circuit 156 for sending and/or receiving information via the antenna 170. The communication circuit 156 can optionally include one or more oscillators, mixers, frequency injectors, etc. to modulate and/or demodulate information on a carrier frequency to be transmitted and/or received by the antenna 170. In some examples, the eye-mountable device 110 is configured to indicate an output from a bio-sensor by modulating an impedance of the antenna 170 in a manner that is perceivable by the external reader 180. For example, the communication circuit 156 can cause variations in the amplitude, phase, and/or frequency of backscatter radiation from the antenna 170, and such variations can be detected by the reader 180.

The controller 150 is connected to the bio-interactive electronics 160 via interconnects 151. For example, where the controller 150 includes logic elements implemented in an integrated circuit to form the sensor interface module 152 and/or display driver module 154, a patterned conductive material (e.g., gold, platinum, palladium, titanium, copper, aluminum, silver, metals, combinations of these, etc.) can connect a terminal on the chip to the bio-interactive electronics 160. Similarly, the controller 150 is connected to the antenna 170 via interconnects 157.

It is noted that the block diagram shown in FIG. 1 is described in connection with functional modules for convenience in description. However, embodiments of the eye-mountable device 110 can be arranged with one or more of the functional modules ("sub-systems") implemented in a single chip, integrated circuit, and/or physical component. For example, while the rectifier/regulator 146 is illustrated in the power supply block 140, the rectifier/regulator 146 can be implemented in a chip that also includes the logic elements of the controller 150 and/or other features of the embedded electronics in the eye-mountable device 110. Thus, the DC supply voltage 141 that is provided to the controller 150 from the power supply 140 can be a supply voltage that is provided to components on a chip by rectifier and/or regulator components located on the same chip. That is, the functional blocks in FIG. 1 shown as the power supply block 140 and controller block 150 need not be implemented as physically separated modules. Moreover, one or more of the functional modules described in FIG. 1 can be implemented by separately packaged chips electrically connected to one another.

Additionally or alternatively, the energy harvesting antenna 142 and the communication antenna 170 can be implemented with the same physical antenna. For example, a loop antenna can both harvest incident radiation for power generation and communicate information via backscatter radiation.

The external reader 180 includes an antenna 188 (or a group of multiple antennas) to send and receive wireless signals 171 to and from the eye-mountable device 110. The external reader 180 also includes a computing system with a processor 186 in communication with a memory 182. The memory 182 can be a non-transitory computer-readable medium that can include, without limitation, magnetic disks, optical disks, organic memory, and/or any other volatile (e.g. RAM) or non-volatile (e.g. ROM) storage system readable by the processor 186. The memory 182 can include a data storage 183 to store indications of data, such as sensor readings (e.g., from the analyte bio-sensor 162), program settings (e.g., to adjust behavior of the eye-mountable device 110 and/or external reader 180), etc. The memory 182 can also include program instructions 184 for execution by the processor 186 to cause the external reader 180 to perform processes specified by the instructions 184. For example, the program instructions 184 can cause external reader 180 to provide a user interface that allows for retrieving information communicated from the eye-mountable device 110 (e.g., sensor outputs from the analyte bio-sensor 162). The external reader 180 can also include one or more hardware components for operating the antenna 188 to send and receive the wireless signals 171 to and from the eye-mountable device 110. For example, oscillators, frequency injectors, encoders, decoders, amplifiers, filters, etc. can drive the antenna 188 according to instructions from the processor 186.

The external reader 180 can be a smart phone, digital assistant, or other portable computing device with wireless connectivity sufficient to provide the wireless communication link 171. The external reader 180 can also be implemented as an antenna module that can be plugged in to a portable computing device, such as in an example where the communication link 171 operates at carrier frequencies not commonly employed in portable computing devices. In some instances, the external reader 180 is a special-purpose device configured to be worn relatively near a wearer's eye to allow the wireless communication link 171 to operate with a low power budget. For example, the external reader 180 can be integrated in a piece of jewelry such as a necklace, earing, etc. or integrated in an article of clothing or an accessory worn near the head, such as a hat, headband, a scarf, a pair of eyeglasses, etc.

In some embodiments, the system 100 can operate to non-continuously ("intermittently") supply energy to the eye-mountable device 110 to power the controller 150 and sensor electronics 160. For example, radio frequency radiation 171 can be supplied to power the eye-mountable device 110 long enough to operate the sensor electronics 160 and communicate an outcome of such operation. In such an example, the supplied radio frequency radiation 171 can be considered an interrogation signal from the external reader 180 to the eye-mountable device 110 to request feedback (e.g., a sensor measurement). By periodically interrogating the eye-mountable device 110 (e.g., by supplying radio frequency radiation 171 to temporarily turn the device on), the external reader 180 can accumulate a set of measurements (or other feedback) over time from the sensor electronics 160 without continuously powering the eye-mountable device 110.

Figure 2A:
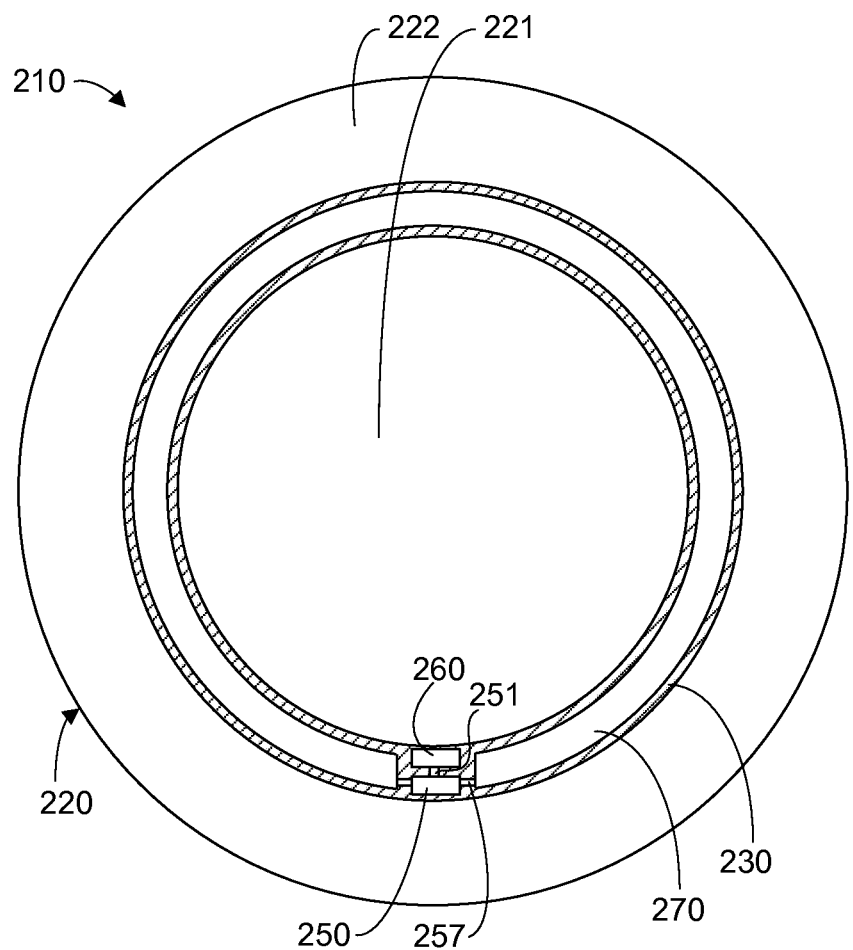
FIG. 2A is a top view of an example eye-mountable device.
Figure 2B:
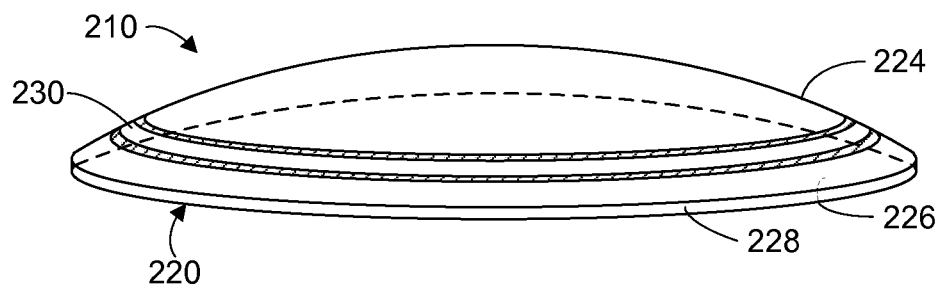
FIG. 2B is a side view of the example eye-mountable device shown in FIG. 2A.

FIG. 2A is a top view of an example eye-mountable electronic device 210 (or ophthalmic electronics platform). FIG. 2B is an aspect view of the example eye-mountable electronic device shown in FIG. 2A. It is noted that relative dimensions in FIGS. 2A and 2B are not necessarily to scale, but have been rendered for purposes of explanation only in describing the arrangement of the example eye-mountable electronic device 210. The eye-mountable device 210 can be formed of a polymeric material 220 shaped as a curved disk. The eye-mountable device 210 includes a loop antenna 270, a controller 250, and a conductivity sensor 260 mounted on a substrate 230 that is embedded in the polymeric material 220.

The polymeric material 220 can be a substantially transparent material to allow incident light to be transmitted to the eye while the eye-mountable device 210 is mounted to the eye. The polymeric material 220 can be a biocompatible material similar to those employed to form vision correction and/or cosmetic contact lenses in optometry, such as polyethylene terephthalate ("PET"), polymethyl methacrylate ("PMMA"), polyhydroxyethylmethacrylate ("polyHEMA"), silicone hydrogels, combinations of these, etc. The polymeric material 220 can be formed with one side having a concave surface 226 suitable to fit over a corneal surface of an eye. The opposite side of the disk can have a convex surface 224 that does not interfere with eyelid motion while the eye-mountable device 210 is mounted to the eye. A circular outer side edge 228 connects the concave surface 226 and convex surface 224. The polymeric material 220 can be formed with a curved shape in a variety of ways. For example, techniques similar to those employed to form vision-correction contact lenses can be employed to form the polymeric material 220, such as heat molding, injection molding, spin casting, etc.

The eye-mountable device 210 can have dimensions similar to a vision correction and/or cosmetic contact lenses, such as a diameter of approximately 1 centimeter, and a thickness of about 0.1 to about 0.5 millimeters. However, the diameter and thickness values are provided for explanatory purposes only. In some embodiments, the dimensions of the eye-mountable device 210 can be selected according to the size and/or shape of the corneal surface of the wearer's eye and/or to accommodate one or more components embedded in the polymeric material 220.

While the eye-mountable device 210 is mounted in an eye, the convex surface 224 faces outward to the ambient environment while the concave surface 226 faces inward, toward the corneal surface. The convex surface 224 can therefore be considered an outer, top surface of the eye-mountable device 210 whereas the concave surface 226 can be considered an inner, bottom surface. The "top" view shown in FIG. 2A is facing the convex surface 224.

The substrate 230 can be embedded in the polymeric material 220 so as to be situated along the outer periphery 222 of the polymeric material 220, away from the central region 221. The substrate 230 can be shaped as a flat, circular ring (e.g., a disk with a centered hole). The flat surface of the substrate 230 (e.g., along the radial width) serves as a platform for mounting electronics such as chips (e.g., via flip-chip mounting) and for patterning conductive materials (e.g., via microfabrication techniques such as photolithography, deposition, plating, etc.) to form electrodes, antenna(e), and/or interconnections. Both the substrate 230 and the polymeric material 220 can be approximately cylindrically symmetric about a common central axis. The substrate 230 can have, for example, a diameter of about 10 millimeters, a radial width of about 1 millimeter (e.g., an outer radius 1 millimeter greater than an inner radius), and a thickness of about 50 micrometers. However, these dimensions are provided for example purposes only, and in no way limit the present disclosure. The substrate 230 can be implemented to assume a variety of different form factors, similar to the discussion of the substrate 130 in connection with FIG. 1 above.

The controller 250 can be a chip including logic elements configured to operate the conductivity sensor 260 and the loop antenna 270. The controller 250 is electrically connected to the loop antenna 270 by interconnects 257 also situated on the substrate 230. Similarly, the controller 250 is electrically connected to the sensor 260 by an interconnect 251. The interconnects 251, 257, the loop antenna 270, and conductive electrodes included in the sensor 260 can be formed from conductive materials patterned on the substrate 230 by a process for precisely patterning such materials, such as deposition, photolithography, etc. The conductive materials patterned on the substrate 230 can be, for example, gold, platinum, palladium, titanium, carbon, aluminum, copper, silver, silver-chloride, conductors formed from noble materials, metals, combinations of these, etc.

The loop antenna 270 is a layer of conductive material patterned along the flat surface of the substrate to form a flat conductive ring. In some examples, to allow additional flexibility along the curvature of the polymeric material, the loop antenna 270 can include multiple substantially concentric sections electrically joined together in parallel or in series. Each section can then flex independently along the concave/convex curvature of the eye-mountable device 210. In some examples, the loop antenna 270 can be formed without making a complete loop. For instances, the antenna 270 can have a cutout to allow room for the controller 250 and the sensor 260, as illustrated in FIG. 2A. However, the loop antenna 270 can also be arranged as a continuous strip of conductive material that wraps entirely around the flat surface of the substrate 230 one or more times. For example, a strip of conductive material with multiple windings can be patterned on the side of the substrate 230 opposite the controller 250 and sensor 260. Interconnects between the ends of such a wound antenna (e.g., the antenna leads) can then be passed through the substrate 230 to the controller 250.

Figure 2D:
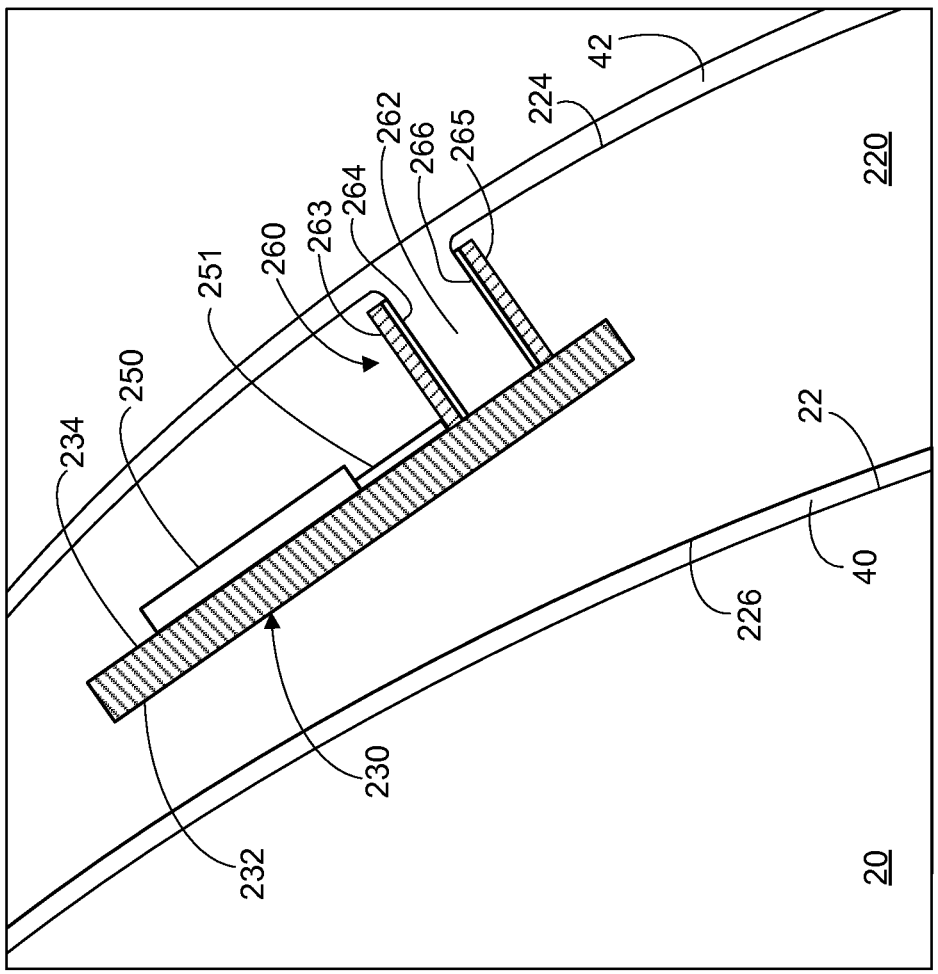
FIG. 2D is a side cross-section view enhanced to show the tear film layers surrounding the surfaces of the example eye-mountable device when mounted as shown in FIG. 2C.
Figure 2C:
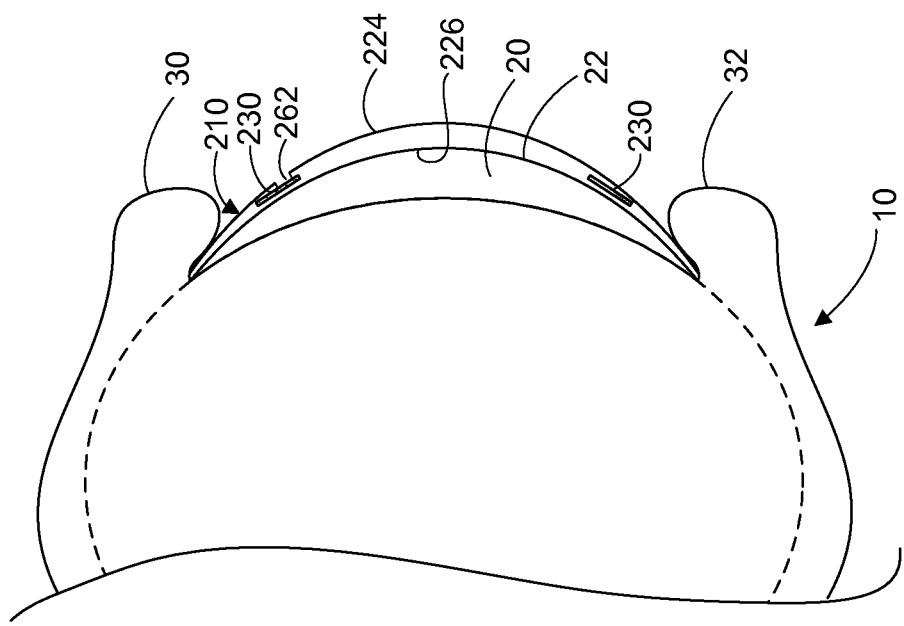
FIG. 2C is a side cross-section view of the example eye-mountable device shown in FIGS. 2A and 2B while mounted to a corneal surface of an eye.

FIG. 2C is a side cross-section view of the example eye-mountable electronic device 210 while mounted to a corneal surface 22 of an eye 10. FIG. 2D is a close-in side cross-section view enhanced to show the tear film layers 40, 42 surrounding the exposed surfaces 224, 226 of the example eye-mountable device 210. It is noted that relative dimensions in FIGS. 2C and 2D are not necessarily to scale, but have been rendered for purposes of explanation only in describing the arrangement of the example eye-mountable electronic device 210. For example, the total thickness of the eye-mountable device can be about 200 micrometers, while the thickness of the tear film layers 40, 42 can each be about 10 micrometers, although this ratio may not be reflected in the drawings. Some aspects are exaggerated to allow for illustration and to facilitate explanation.

The eye 10 includes a cornea 20 that is covered by bringing the upper eyelid 30 and lower eyelid 32 together over the top of the eye 10. Incident light is received by the eye 10 through the cornea 20, where light is optically directed to light-sensing elements of the eye 10 (e.g., rods and cones, etc.) to stimulate visual perception. The motion of the eyelids 30, 32 distributes a tear film across the exposed corneal surface 22 of the eye 10. The tear film is an aqueous solution secreted by the lacrimal gland to protect and lubricate the eye 10. When the eye-mountable device 210 is mounted in the eye 10, the tear film coats both the concave and convex surfaces 224, 226 with an inner layer 40 (along the concave surface 226) and an outer layer 42 (along the convex layer 224). The tear film layers 40, 42 can be about 5 to 10 micrometers in thickness and together account for about 5 to 10 microliters.

The tear film layers 40, 42 are distributed across the corneal surface 22 and/or the convex surface 224 by motion of the eyelids 30, 32. For example, the eyelids 30, 32 may raise and lower, respectively, to spread a small volume of tear film across the corneal surface 22 and/or the convex surface 224 of the eye-mountable device 210. The tear film layer 40 on the corneal surface 22 also facilitates mounting the eye-mountable device 210 by capillary forces between the concave surface 226 and the corneal surface 22.

As shown in the cross-sectional views in FIGS. 2C and 2D, the substrate 230 can be inclined such that the flat mounting surfaces of the substrate 230 are approximately parallel to an adjacent portion of the convex surface 224. The substrate 230 can be a flattened ring with an inward-facing surface 232 (closer to the concave surface 226 of the polymeric material 220) and an outward-facing surface 234 (closer to the convex surface 224). The substrate 230 can have electronic components and/or patterned conductive materials mounted to either or both mounting surfaces 232, 234. As shown in FIG. 2D, the conductivity sensor 260, controller 250, and conductive interconnect 251 are mounted on the outward-facing surface 234. However, the electronics, electrodes, etc. situated on the substrate 230 can be mounted to either the "inward" facing side 232 or the "outward" facing side 234. Moreover, in some embodiments, some electronic components can be mounted on one side (e.g., 232), while other electronic components are mounted to the opposing side (e.g., 234), and connections between the two sides can be made through conductive materials passing through the substrate 230.

The conductivity sensor 260 includes two electrodes 264, 266 mounted on frame components 263, 265. The electrodes 264, 266 are connected to the controller 250 via the interconnect 251. For example, each electrode 264, 266 may be electrically connected to a substrate-facing conductive pad (e.g., integrally formed on the frame components 263, 265) that makes contact with corresponding conductive pads formed on the substrate 230 when the sensor 260 is positioned on the substrate 230. The frame components 263, 265 extend normal from the outward-facing mounting surface 234 of the substrate 230. The electrodes 264, 266 are formed on the sidewalls of the frame components 263, 265 such that the electrodes each have a height that extends perpendicular to the plane of the substrate 230 (and to the adjacent portion of the convex surface 224 and the tear film layer 42 situated thereon). In some examples, the height of the sample volume 262 (e.g., the height of the electrodes 264, 266) may be greater than the thickness of the tear film coating 42, and may be several times the thickness of the tear film outer layer 42. For example, the depth of the sample volume 262, in a direction perpendicular to the locally proximate region of the outer layer 42 of tear film may be greater than 50 micrometers, whereas the tear film outer layer may be about 5 to 10 micrometers in thickness. As a result, the sample volume 262 may be relatively insensitive to variations in tear film thickness, which may influence the field locally surrounding the electrodes 264, 266, for example.

The two electrodes 264, 266 define opposite sides of a sample volume 262 of the conductivity sensor 260. The sample volume 262 (or sample cell), is bounded by the two electrodes 264, 266. For example, the electrodes 264, 266 and/or frame components 263, 265 can define sidewalls of a trench, and the trench can be a fluid sample volume for the conductivity sensor 260. A channel formed on the convex surface 224 can expose the sample volume 262 to tear fluid from the outer layer 42. Thus, while mounted to the corneal surface 22, the sample volume 262 can be occupied by tear fluid from the outer layer 42 coating the convex surface 224, and the conductivity of the tear fluid can be measured using the sensor 260. In practice, the controller 250 can apply a voltage to the electrodes 264, 266, and measure the current through the electrodes 263, 265. The controller 250 can use the antenna 270 to communicate an indication of the measurement result (e.g., an indication of the measured current) to an external reader. The applied voltage and measured current can be used to determine the conductivity of the tear fluid occupying the sample volume 262.

For a given applied voltage, an elevated current measure indicates a relatively greater conductivity, which corresponds to a greater ionic concentration of the tear fluid (and, by extension, a greater osmolarity). The measurement results communicated by the eye-mountable device 210 may be used to determine an osmolarity. Such a determination may be based in part on look-up tables that map sensor measurements to osmolarity values and/or based on calibration information that establish a relationship between one or more sensor measurements and known osmolarity readings. Moreover, the conductivity measurement may be calibrated for temperature to account for variation with temperature in the conductance of the fluid in sample volume 262.

The channel that exposes the sample volume 262 of the sensor 260 may be formed by a variety of techniques, including plasma etching the polymeric material 230. In other examples, the polymeric material 230 may be configured to absorb solutes from the tear film and allow the solutes to diffuse through the polymeric material to the region between the sensor electrodes 264, 266. The diffused solutes may then influence the ion concentration in the sample region and thereby facilitate a conductivity measurement. The tear film conductivity (and by extension, osmolarity) can then be estimated based on such a conductivity measurement.

III. Body-Mountable Fluid Conductivity Sensor

Figure 3A:
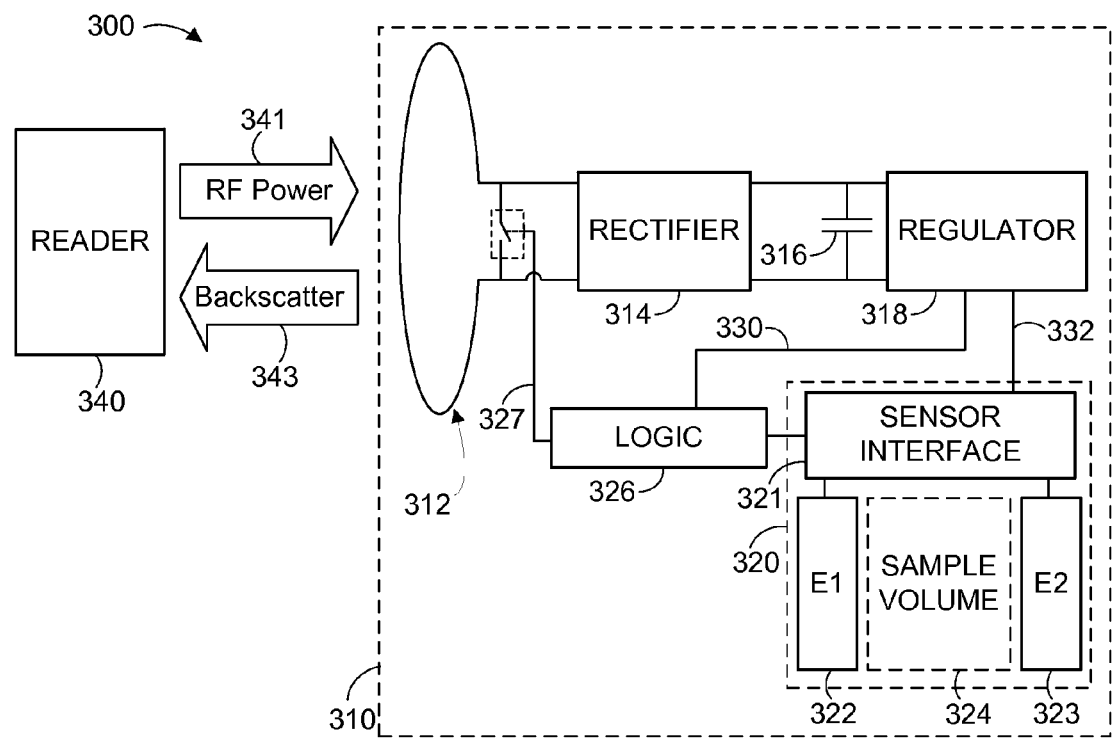
FIG. 3A is a functional block diagram of an example system configured to measure conductivity of a fluid sample.

FIG. 3A is a functional block diagram of a system 300 configured to measure fluid conductivity. The system 300 includes a body-mountable device 310 with embedded electronic components powered by an external reader 340. In one example, the body-mountable device 310 may be the same or similar to the eye-mountable devices 110, 210 described above. The body-mountable device 310 may also be implemented in a form factor configured to be mounted to other body locations so as to access sample fluids in-vivo, including implantable configurations. The body-mountable device 310 may therefore include an encapsulating biocompatible polymeric material in which electronics are embedded, and which includes one or more mounting surfaces. In some examples, the body-mountable device 310 may include a mounting surface configured to be mounted to a tooth, a skin surface, a mucous membrane, upon a subcutaneous region, within an interstitial region, or in another region in which in-vivo fluid conductivity may be measured.

The body-mountable device 310 includes an antenna 312 for capturing radio frequency radiation 341 from the external reader 340. The body-mountable device 310 includes a rectifier 314, an energy storage 316, and regulator 318 for generating power supply voltages 330, 332 to operate the embedded electronics. The body-mountable device 310 includes a conductivity sensor 320 with a first electrode 322 and a second electrode 323 driven by a sensor interface 321. The sensor electrodes 322, 323 are situated to form boundaries of a sample volume 324, which can be occupied by a fluid sample. The body-mountable device 310 includes hardware logic 326 for communicating results from the sensor 320 to the external reader 340 by modulating the impedance of the antenna 312. An impedance modulator 327 (shown symbolically as a switch in FIG. 3A) can be used to modulate the antenna impedance according to instructions from the hardware logic 326.

The conductivity sensor 320 measures conductivity by applying a voltage to the electrodes 322, 323 and measuring a current. The applied voltage could be, for example, an AC voltage that is generated by an AC voltage generator in the sensor interface 321. In response to the applied voltage, fluid occupying the sample volume 324 conducts current between the electrodes 322, 323, and the current can be measured using a current sensor in the sensor interface 321. The measured current depends on the ion concentration in the fluid occupying the sample volume 324, and the ion concentration in turn is related to the solute concentration. Thus, the measured current (or conductivity) can be used to estimate the osmolarity of the fluid in the sample volume 324.

Figure 3B:
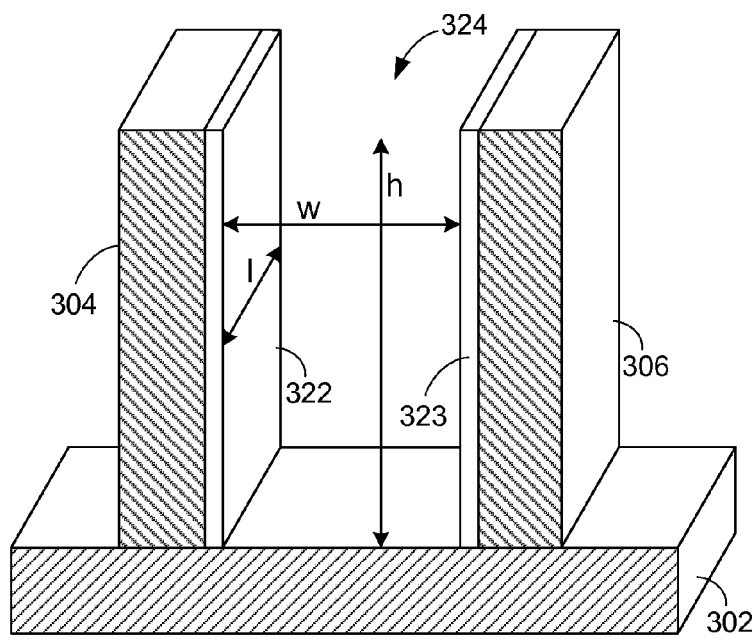
FIG. 3B illustrates an example conductivity sample volume.

FIG. 3B illustrates an example conductivity sample volume 324. The electrodes 322, 323 may be situated along sidewalls of frame components 304, 306, which each extend normal from a substrate 302 that is embedded in the body-mountable device 310. The sample volume 324 is a three-dimensional region with a height (labelled "h" in FIG. 3B) that extends normal to the substrate 302, a width (labelled "w" in FIG. 3B) that extends between the two electrodes 322, 323, and a length (labelled "l" in FIG. 3B) that extends along the electrodes 322, 323 parallel to the substrate 302. The sidewalls of the two frame components 304, 306 and the electrodes 322, 323 disposed thereon can be arranged such that locally proximate, facing sections of each electrode 322, 323 are substantially parallel to one another. In addition, the two frame components 304, 306 (and electrodes 322, 323) can be arranged such that the separation distance between the two electrodes (i.e., the width "w") is substantially constant throughout the sample volume 324 along the entire length and height.

The total volume of the sample volume 324 is therefore given by the product of the length, width, and height. In one example, the width may be about 50 micrometers, the height may be about 60 micrometers, and the length may be about 3000 micrometers, which corresponds to a sample volume of about 9 nanoliters. By way of comparison, the total volume of tear fluid coating an eye is about 5 to 10 microliters, so the sample volume 324 may be much smaller than the total volume of tear fluid. The length, width, and height dimensions provided above are included for purposes of explanation only. In some examples, the height may be between 50 and 100 micrometers; the width may be less than 100 micrometers, and the length may be such that the total volume may be less than about 100 nanoliters. Other dimensions are also possible.

The two frame components 304, 306 may be sidewalls of a trench structure that is mounted on the substrate 302. The electrodes 322, 323 may then be formed by patterning a conductive material over the trench so as to coat the two sidewalls. An example fabrication technique is described in connection with FIG. 6 below.

In some examples, the sensor interface 321 is configured to apply an AC voltage to the electrodes 322, 323, which helps mitigate the effects of polarizing the sample volume 324. For example, if a DC voltage is applied, ions in the sample volume 324 migrate to the electrode surface. The accumulation of ions and also the occurrence of electrochemical reactions at the electrode surface in such an example bias the sensor results by introducing a polarization resistance. Thus, the sensor interface 321 can, for example, apply an AC voltage between the sensor electrodes 322, 323, and measure the current via one or both electrodes 322, 323. Thus, the sensor interface 321 may include an AC voltage generator that is powered by the voltage 332 from the regulator 318. Upon making a current measurement, the sensor interface 321 provides an output to the hardware logic 326, which causes the antenna 312 to indicate the measured current to the reader 340 using backscatter radiation 343.

The rectifier 314, energy storage 316, and voltage regulator 318 can operate to harvest energy from received radio frequency radiation 341. The radio frequency radiation 341 causes radio frequency electrical signals on leads of the antenna 312. The rectifier 314 is connected to the antenna leads and converts the radio frequency electrical signals to a DC voltage. The energy storage 316 (e.g., capacitor) is connected across the output of the rectifier 314 to filter out high frequency components of the DC voltage from the rectifier 314. The regulator 318 receives the DC voltage and outputs supply voltages 330, 332 to operate the hardware logic 324 and the conductivity sensor 320. The digital supply voltages 330, 332 may be voltages suitable for driving digital logic circuitry, such as approximately 1.2 volts, approximately 3 volts, etc. Reception of the radio frequency radiation 341 from the external reader 340 (or another source, such as ambient radiation, etc.) causes the supply voltages 330, 332 to be supplied to the sensor 320 and hardware logic 324. While powered, the sensor 320 and hardware logic 324 are configured to generate and measure a current indicative of conductance (and, by extension, osmolarity) and communicate the results.

The external reader 340 associates the backscatter signal 343 with the sensor result (e.g., according to a pre-programmed relationship associating impedance of the antenna 312 with output from the sensor 320 using look-up tables, calibration information, etc.). The reader 340 can then store the indicated sensor results (e.g., conductivity values and/or osmolarity values) in a local memory and/or an external memory (e.g., by communicating with the external memory through a network).

In some embodiments, one or more of the features shown as separate functional blocks can be implemented ("packaged") on a single chip. For example, the eye-mountable device 310 can be implemented with the rectifier 314, energy storage 316, voltage regulator 318, sensor interface 321, and the hardware logic 324 packaged together in a single chip or controller module. Such a controller can have interconnects ("leads") connected to the loop antenna 312 and the sensor electrodes 322, 323. Such a controller operates to harvest energy received at the loop antenna 312, apply a voltage between the electrodes 322, 323 sufficient to develop an amperometric current, measure the amperometric current, and indicate the measured current via the antenna 312 (e.g., through the backscatter radiation 343).

Figure 4A:
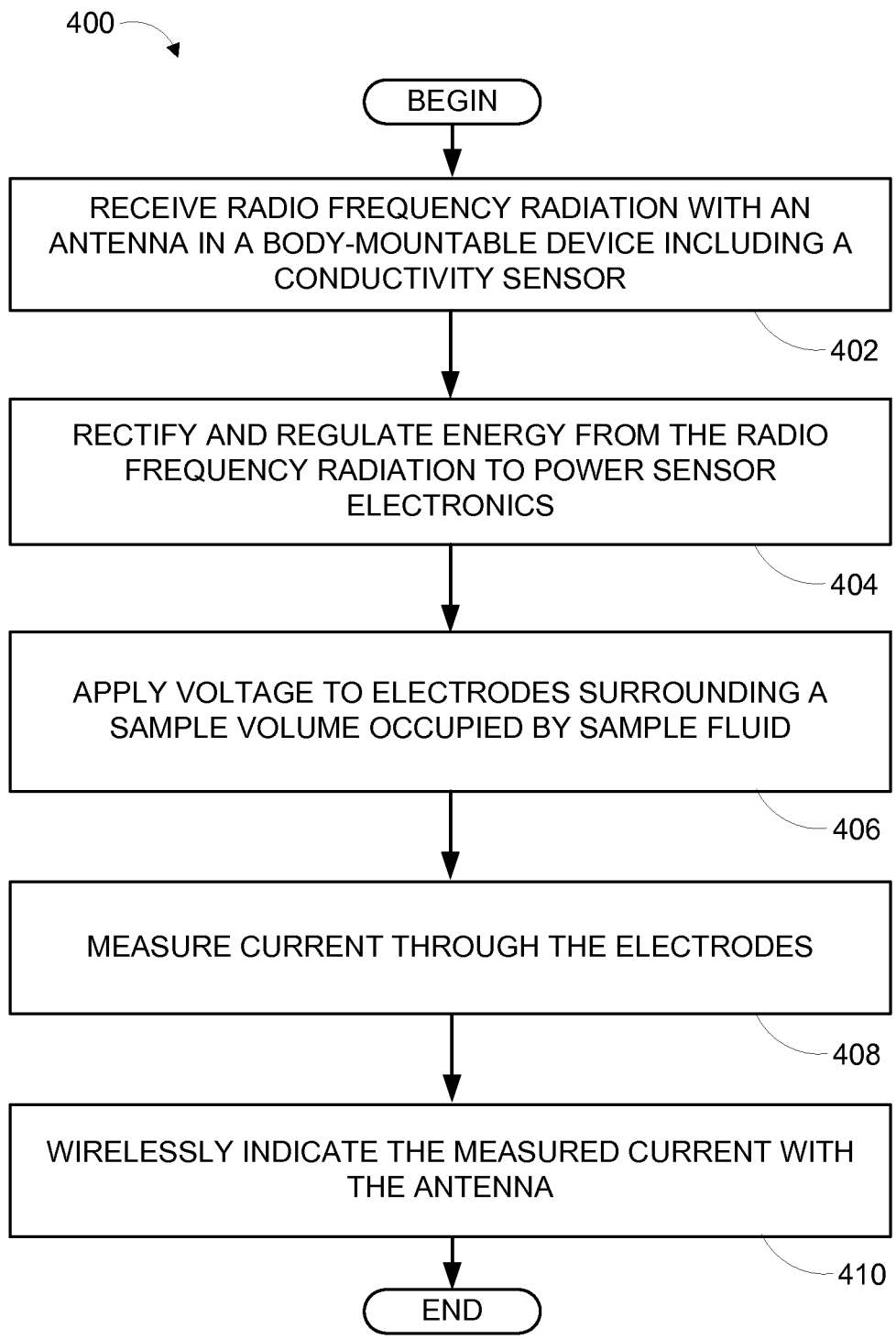
FIG. 4A is a flowchart of an example process for operating a sensor in a body-mountable device to measure fluid conductivity.

FIG. 4A is a flowchart of an example process 400 for operating a sensor in a body-mountable device to measure tear film conductivity. Radio frequency radiation is received at an antenna in a body-mountable device including an embedded conductivity sensor (402). Electrical signals due to the received radiation are rectified and regulated to power the conductivity sensor and associated controller (404). For example, a rectifier and/or regulator can be connected to the antenna leads to output a DC supply voltage for powering the conductivity sensor, controller, and/or other bio-interactive electronics. A voltage is applied to electrodes surrounding a sample volume occupied by sample fluid (406). For example, an AC voltage sufficient to cause current to flow through the sample fluid (e.g., via ionic migration) may be applied to the electrodes. A current is measured through the electrodes surrounding the sample volume (408). For example, a controller may apply a voltage to the electrodes while measuring the resulting current. The measured current is wirelessly indicated with the antenna (410). For example, backscatter radiation can be manipulated to indicate the sensor result by modulating the antenna impedance.

Figure 4B:
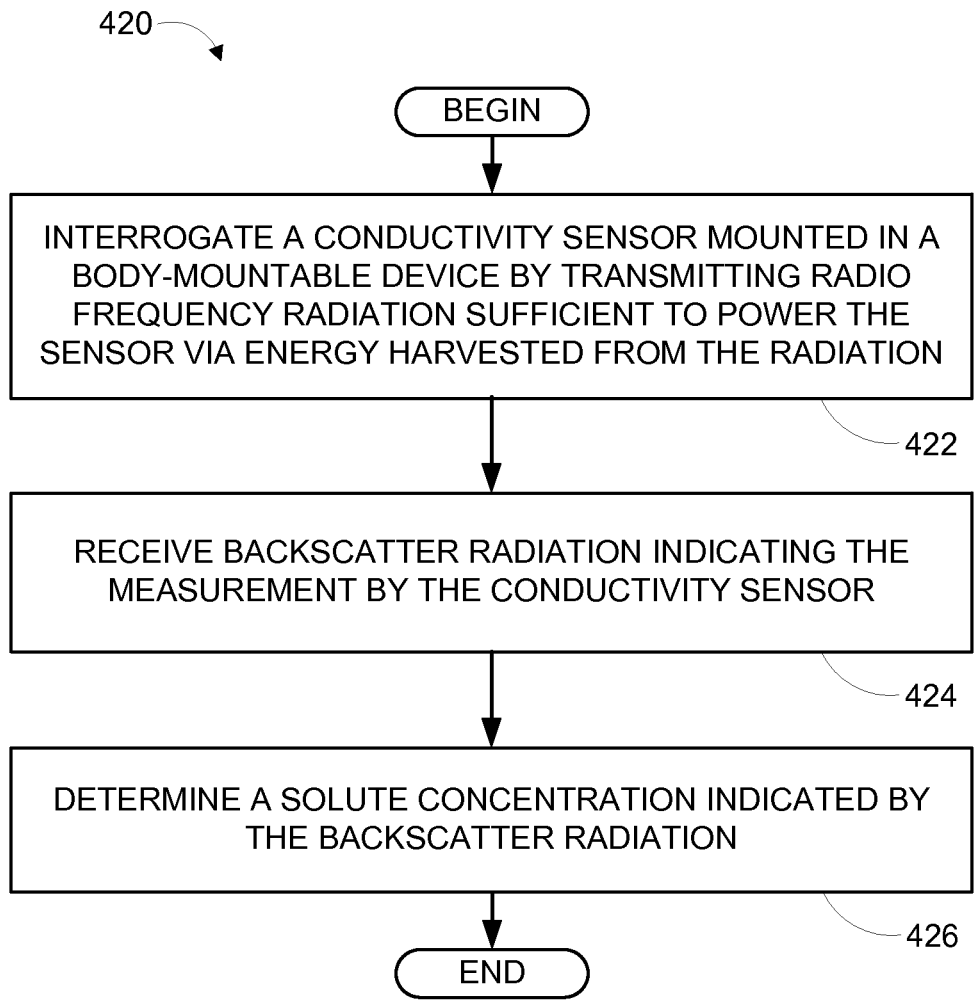
FIG. 4B is a flowchart of an example process for operating an external reader to interrogate a conductivity sensor in a body-mountable device to measure fluid conductivity and determine osmolarity.

FIG. 4B is a flowchart of an example process 420 for operating an external reader to interrogate a conductivity sensor in a body-mountable device to measure fluid conductivity and determine osmolarity. Radio frequency radiation is transmitted to a conductivity sensor mounted in a body-mountable device from the external reader (422). The transmitted radiation can be sufficient to power the sensor to perform a measurement and communicate the results (422). For example, the radio frequency radiation used to power the electrochemical sensor can be similar to the radiation 341 transmitted from the external reader 340 to the body-mountable device 310 described in connection with FIG. 3A above. The external reader then receives backscatter radiation indicating the measurement by the conductivity sensor (424). For example, the backscatter radiation can be similar to the backscatter signals 343 sent from the body-mountable device 310 to the external reader 340 described in connection with FIG. 3A above. The backscatter radiation received at the external reader is then associated with an osmolarity value (426). In some cases, the determined osmolarity value can be stored in the external reader memory and/or a network-connected data storage.

For example, the sensor result (e.g., the measured current) can be encoded in the backscatter radiation by modulating the impedance of the backscattering antenna. The external reader can detect the antenna impedance and/or change in antenna impedance based on a frequency, amplitude, and/or phase shift in the backscatter radiation. The sensor result can then be extracted by associating the impedance value with the sensor result by reversing the encoding routine employed within the eye-mountable device. Thus, the reader can map a detected antenna impedance value to a measured current value. The current value can then be associated with an osmolarity value based on a look-up table or a predetermined relationship (e.g., a calibration relationship). In some cases, the determination of an osmolarity value may account for various factors that influence the scaling between osmolarity and measured current, including the temperature of the sample fluid, the magnitude of the applied AC voltage, the frequency of the applied AC voltage, and/or the form factor of the sample volume (e.g., ratio of electrode separation to electrode area, etc.).

Figure 5A:
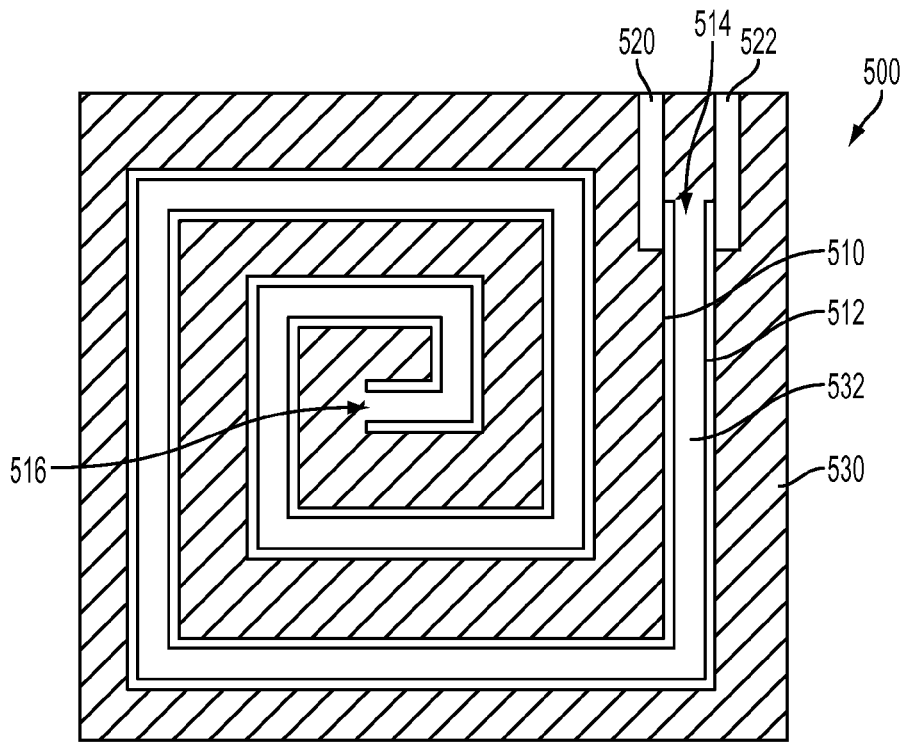
FIG. 5A shows a top view of an example embodiment of a conductivity sensor with electrodes formed along sidewalls of a trench.

FIG. 5A shows a bottom view of an example embodiment of a conductivity sensor 500 with electrodes 510, 512 formed along sidewalls of a trench 532. The trench 532 is formed in a substrate 530 to provide substantially parallel sidewalls for supporting the electrodes 510, 512. The substrate 530 may be a silicon wafer, for example. The electrodes 510, 512 may be formed of a conductive material (e.g., platinum, palladium, gold, sliver, combinations of these, etc.) deposited on the sidewalls of the trench 532. The trench has a length that extends in a coiled fashion from a first end 514 to a second end 516. The total volume of the trench 532 (e.g., product of length, width, and height) may be less than 100 nanoliters, such as about 10 nanoliters. Along the entire length of the trench 532, the two electrodes 510, 512 have a substantially constant separation distance (e.g., width of the trench), which may be about 50 micrometers. The depth of the trench 532, and thus height of the electrodes 510, 512, is also substantially even along the entire length, and may be between about 50 and 100 micrometers. The two electrodes 510, 512 can be formed from a substantially continuous strip of conductive metal along the two internal facing sidewalls in the substrate 530. The electrodes 510, 512 can also be electrically connected to respective mounting pads 520, 522, which may be integrally formed with the electrodes 510, 512 formed on the sidewalls. The connection pads 520, 522 allow the conductivity sensor 500 to electrically connect to corresponding connection pads on a substrate to which the conductivity sensor 500 is mounted. Thus, the bottom view shown in FIG. 5A depicts the side of the sensor 500 that is mounted to a substrate.

Figure 5B:
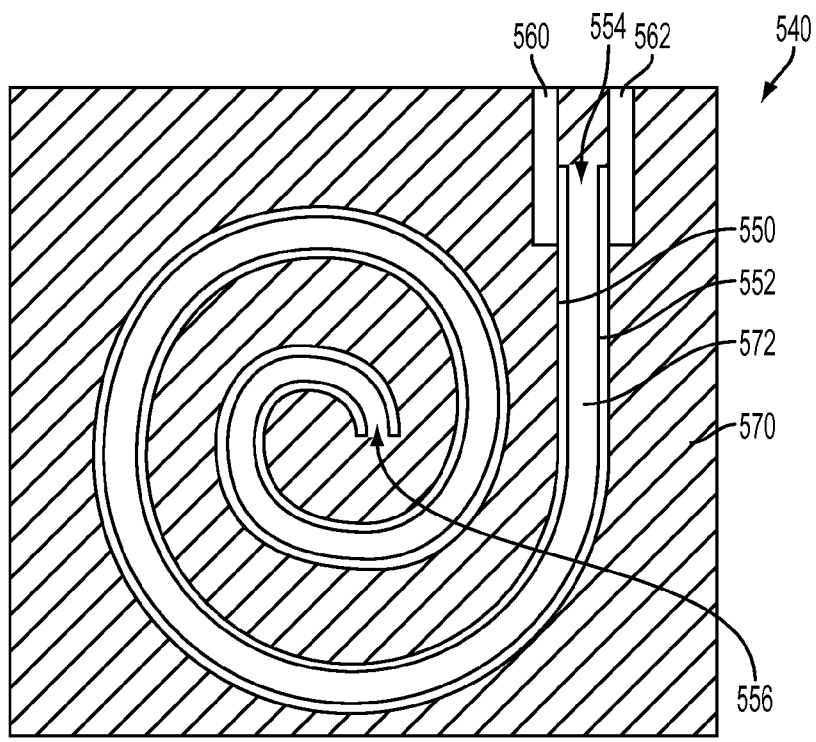
FIG. 5B shows a top view of another example embodiment of a conductivity sensor with electrodes formed along sidewalls of a trench.

FIG. 5B shows a bottom view of another example embodiment of a conductivity sensor 540 with electrodes 550, 552 formed along sidewalls of a trench 572. Similar to the conductivity sensor 500 of FIG. 5A, the trench 572 is also formed in a substrate 570, and extends along a length from one end 556 to another end 554, where the two electrodes 550, 552 are electrically connected to conductive mounting pads 560, 562. The total volume, height, width, and length of the trench 572 may be the same or similar to the dimensions of the trench 532 of the sensor 500. However, in contrast to the conductivity sensor 500 described in connection with FIG. 5A, the conductivity sensor 540 in FIG. 5B is implemented with a curved, coiled form factor. The curved form factor of the sensor 540 may allow for a more constant separation distance (e.g., trench width) between the facing electrodes 550, 552 due to the lack of sharp corners. As a result, the separation distance between locally proximate portions of the facing electrodes 560, 562 may be substantially constant across the length of the trench 572. The absence of corners also reduces field effects that may be associated with corners. Such effects may, for example, be associated with a locally enhanced field strength that may skew conductivity measurements in the regions surrounding the corners.

Substantially constant separation distance between the electrodes in the sensor (electrodes 510, 512 in sensor 500 or electrodes 550, 552 in sensor 540) can provide for more accurate and repeatable conductivity measurements. If the separation distance is not constant, then the conductivity measurement (i.e., the current measurement) may be dominated by current across the portion(s) of the sample volume where the separation distance is smallest, rather than a measure of current that equally weights contributions across the entire sample volume.

IV. Assembly of an Example Conductivity Structure

Figure 6A:
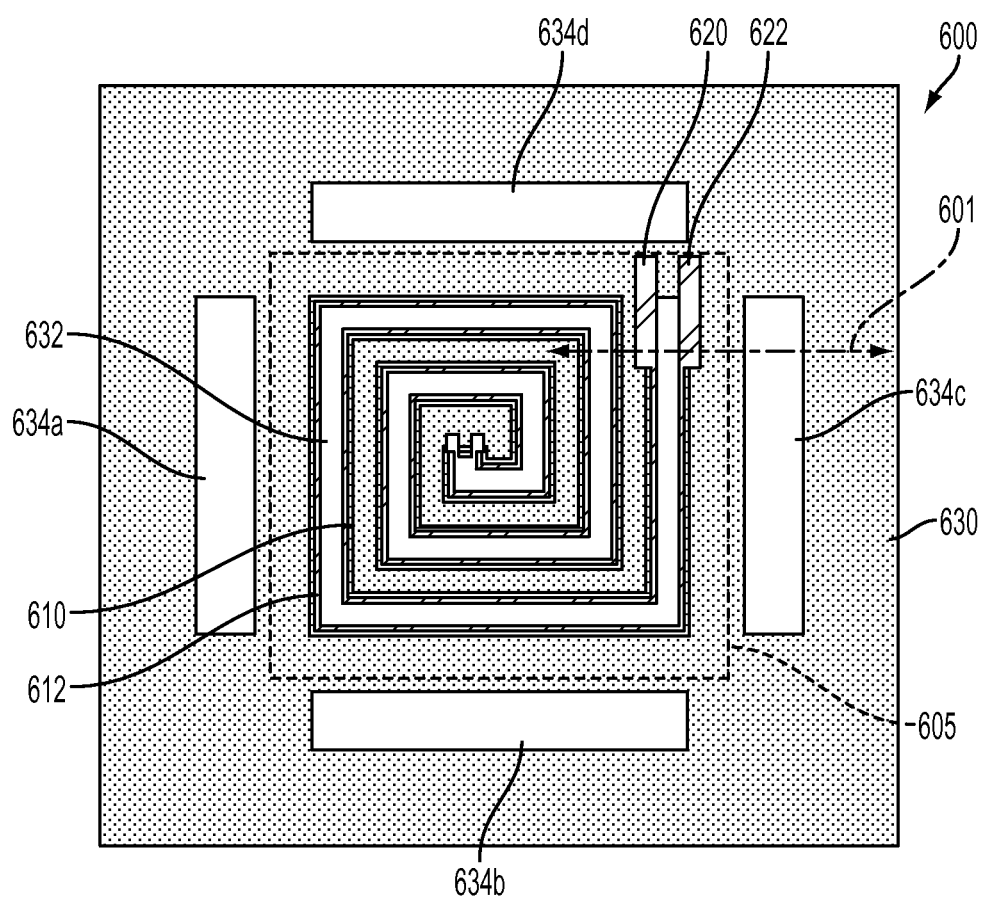
FIG. 6A is a top view of the conductivity sensor during fabrication, according to an example embodiment.

FIG. 6A is a top view of a conductivity sensor 600 during fabrication, according to an example embodiment. The conductivity sensor 600 may be similar in some respects to the conductivity sensor 500 described above in connection with FIG. 5A. The conductivity sensor 600 includes a trench 632 formed in a substrate 630. The substrate may be, for example, a silicon wafer. The trench 632 defines a sample volume that can be occupied by a fluid. Facing electrodes 610, 612 are arranged on the sidewalls of the trench 632 such that the electrodes 610, 612 are situated on opposite sides of the sample volume. The trench 632 extends in a coiled fashion, similar to the trench 532 of the conductivity sensor 500 described in connection with FIG. 5A. Two connection pads 620, 622 are electrically connected to the two electrodes 610, 612 to facilitate mounting the conductivity sensor 600 to corresponding conductive pads (e.g., flip chip mounting). As shown in FIG. 6A, the substrate also includes channels 634*a-d* formed in the substrate 630 adjacent to the trench 632. Each of the channels 634*a-d* extends in a direction that is locally parallel to a portion of the trench 632. As will be described below, the adjacent channels 634*a-d* facilitate removal of the sensor 600 from the substrate 630. For example, after the sensor 600 is fabricated in the substrate 630, the substrate 630 may be diced along the cut pattern 605. Cavities formed below each of the adjacent channels 634*a-d* by an isotropic etchant expand to join with cavities also formed below the trench 632 by the etchant, and the diced structure including the sensor 600 can be separated from the substrate 630 (e.g., the wafer).

FIGS. 6B-6N show cross-sectional views of stages of fabricating a conductivity sensor, according to an example embodiment. The cross-sectional views in FIGS. 6B-6N illustrate fabrication of the example sensor 600 shown in FIG. 6A, taken along the cross-sectional view line 601 shown in FIG. 6A. The illustrations shown in FIGS. 6B-6N are generally shown in cross-sectional views (along the line 601) to illustrate sequentially formed layers developed to create the trench structure and electrodes for the conductivity sensor 600. Layers of photo-resists, conductive materials, and the like can be developed by microfabrication and/or manufacturing techniques such as, for example, electroplating, photolithography, deposition, and/or evaporation fabrication processes and the like. In addition, various stages employ the use of directional and isotropic etchants, and selectively etchable materials. The various materials may be formed according to patterns using photoresists and/or masks to pattern materials in particular arrangements, such as to form wires, electrodes, connection pads, etc. However, the dimensions, including relative thicknesses, of the various layers and structures illustrated and described in connection with FIGS. 6B-6N are not illustrated to scale. Instead, the drawings in FIGS. 6B-6N schematically illustrate the ordering of the various layers for purposes of explanation only.

Figure 6B:
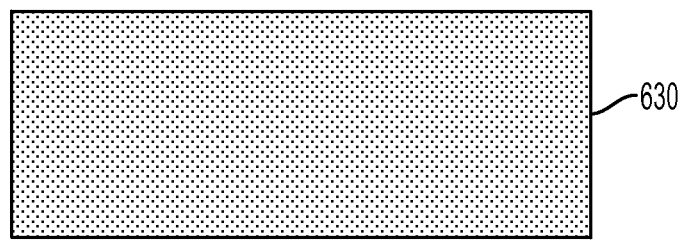
FIGS. 6B-6N show cross-sectional views of stages of fabricating a conductivity sensor, according to an example embodiment.

FIG. 6B illustrates a working substrate 630. The working substrate 630 can have a substantially flat surface suitable for receiving layers of material by deposition, photolithography, etc. For example, the working substrate 630 can be a wafer (e.g., a silicon wafer) similar to those used in the fabrication of semiconductor device and/or microelectronics. The working substrate 630 may be a semiconductive material arranged in a crystalline structure (e.g., silicon). For example, the working substrate 630 may be a silicon wafer with a polished surface, and may have a thickness of about 500 micrometers.

Figure 6C:
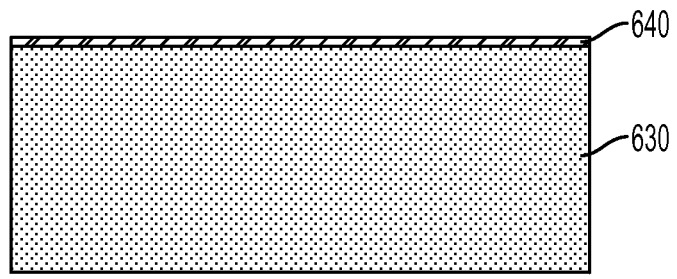

FIG. 6C illustrates a layer 640 formed over the working substrate 630. The layer 640 may include silicon dioxide ($SiO_2$) or another selectively etchable material that is resistant to etching by an isotropic etchant (e.g., $XeF_2$) but susceptible to reactive ion etching. The layer 640 can be formed via chemical vapor deposition and cured or uncured and may have a thickness of about 1 micrometer, for example.

Figure 6D:
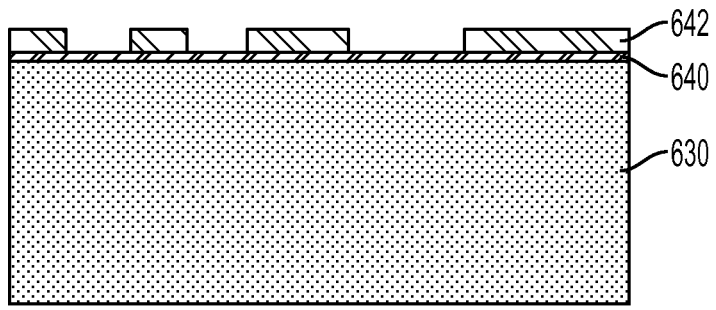

FIG. 6D illustrates a positive photoresist layer 642 patterned over the etch-resistant layer 640. The photoresist layer 642 may be patterned by photolithography, using masks, or another technique. The photoresist layer 642 may be formed of a microelectronic chemical suitable, for example, of AZ-4620, patterned with a thickness of 5 micrometers. Another active photoresist may also be used. The photoresist layer 642 can be patterned over areas of the substrate 630 where trenches are not desired. That is, the areas that do not receive the photoresist layer 642 may be areas where trenches are created in a subsequent fabrication operation.

Figure 6E:
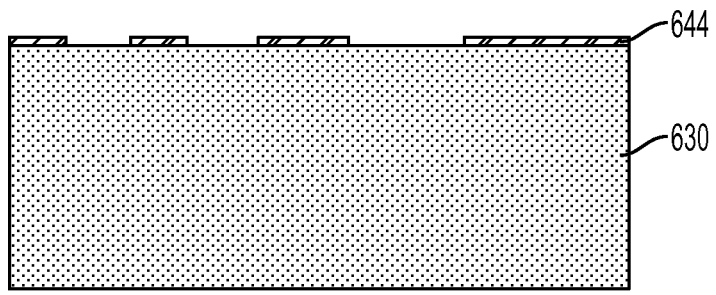

FIG. 6E illustrates the remaining pattern of the layer 644 after etched with reactive ion etching (RIE). The areas of the layer 640 that were covered by the patterned photoresist layer 642 (in FIG. 6D) remain in the pattern 644. The photoresist layer 642 can then be stripped away (e.g., by rinsing with acetone). In an example in which the material of layer 640 is $SiO_2$, reactive ion etching using $CF_4/O_2$ may be used to etch through the $SiO_2$. The areas under the photoresist layer 642 remain following the RIE operation, which results in the patterned layer 644.

Figure 6F:
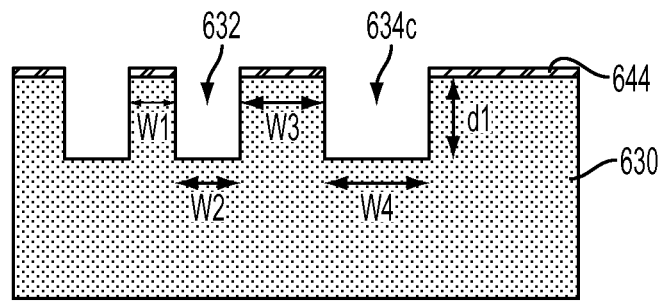

FIG. 6F illustrates the formation of trenches 632, 634c in the substrate 630 in the regions exposed by the pattern 644. The trenches can be formed, for example, by anisotropic deep reactive ion etching (DRIE) using $BCl_3/Cl_2$. The trenches 632, 634c may be formed to a depth d1 of about 60 micrometers, for example. The depth d1 of the trenches may be controlled based on the duration of the DRIE application, for example. The width W1 indicates the separation between adjacent sections of the trench 632 due to the coiled configuration of the trench 632, and may be about 30 micrometers. The width W2 of the trench 632 may be about 50 micrometers. The separation distance W3 between the trench 632 and the adjacent trench 634c may be about 60 micrometers. The width W4 of the adjacent trench 634c may be about 100 micrometers. The dimensions provided above are included for example purposes only. Other example dimensions may also be used, including dimensions that are rations of the example values given above, as well as other values.

Figure 6G:
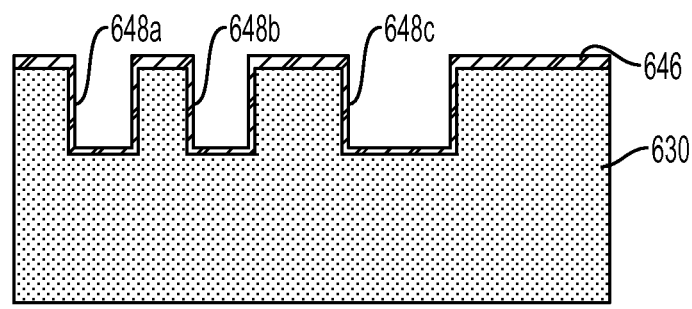

FIG. 6G illustrates a layer 646 following application of additional material over the pattern 644. The additional material could be the same selectively etchable material used to form layer 640, i.e., a material such as $SiO_2$ that is resistant to an isotropic etchant but susceptible to reactive ion etching. The additional material may be formed over the pattern 644 via chemical vapor deposition. The resulting layer 646 may have a substantially uniform thickness over exposed surfaces of the trenches 632, 634c. For example, the thickness of layer 646 on the sidewalls 648a-c and base of the trenches 632, 634c may be about 0.5 micrometers. The layer 646 may have a thickness of about 1.5 micrometers in the areas previously occupied by the pattern 644.

Figure 6H:
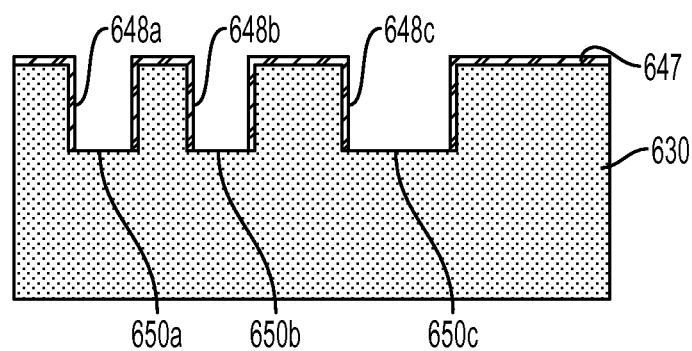

FIG. 6H illustrates another pattern of material 647 following reactive ion etching (RIE) to expose the trench bottoms 650a-c. In an example in which the material of layer 646 is $SiO_2$, reactive ion etching using $CF_4/O_2$ may be used to etch through the $SiO_2$ to both expose the bases 650a-c of the trenches 632, 634c (this may also decrease the thickness of the material remaining in the non-trench areas). The RIE operation may provide an anisotropic removal of the material, and may be applied from a direction substantially normal to the working substrate 630 such that the material on the sidewalls 650a-c is substantially undisturbed by the RIE operation. Thus, following the RIE operation, the sidewalls 650a-c of the trenches and the non-trench areas of the substrate 630 are covered by the material of pattern 647, while the bases of the trenches 632, 634c are exposed.

Figure 6I:
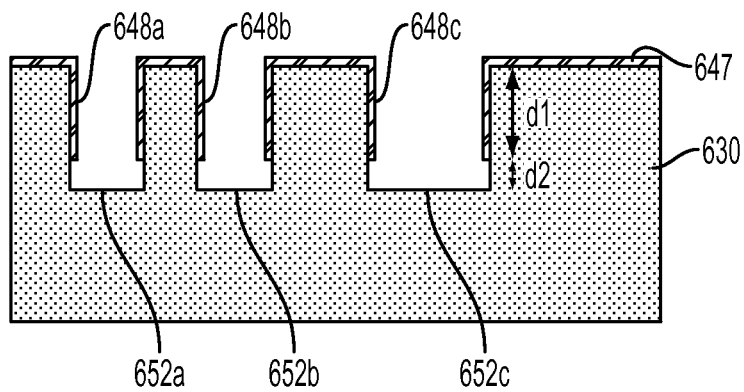

FIG. 6I illustrates a second trench formation operation. After exposing the bases of the trenches 632, 634c, anisotropic DRIE can be used to increase the depth of the trenches 632, 634c (e.g., using $BCl_3/Cl_2$). The increased depth d2 can be, for example, about 20 micrometers.

Figure 6J:
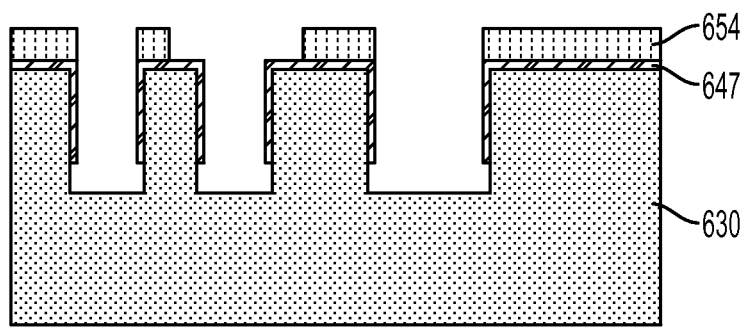

FIG. 6J illustrates a negative photoresist layer 654 patterned over the pattern 647. The negative photoresist layer 654 may be, for example, NR9 and may be patterned using a mask with a thickness of about 6 micrometers. The negative photoresist 654 may be lifted from the substrate 630 in a subsequent step, and thereby re-expose the areas the negative photoresist 654 is patterned over.

Figure 6K:
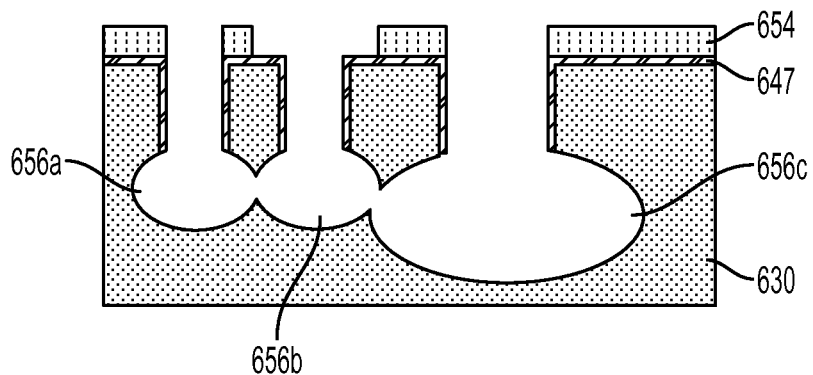

FIG. 6K illustrates cavities 656a-c formed by an isotropic etchant applied to the exposed bases 652a-c of the trenches 632, 634c. For example, the exposed silicon may be etched by an isotropic vapor-phase etch using $XeF_2$. The materials of pattern 647 and negative photoresist 654 may be resistant to the isotropic etchant, such that the areas covered by those materials are undisturbed. The cavities 656a-c created in the working substrate 630 by the isotropic etchant may be allowed to expand large enough to join together, as shown in FIG. 6K. Allowing the cavities 656a-c to join together during the isotropic etching facilitates removal of the trench structure from the working substrate 630 upon completion of the sensor 600.

Figure 6L:
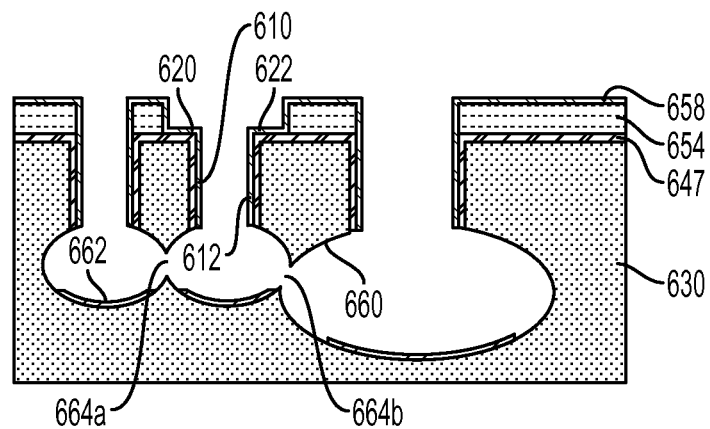

FIG. 6L illustrates a conductive layer 658 formed over the trench structure. The conductive layer 658 may be formed by sputtering a layer of palladium and gold with thicknesses of 20 nanometers and 200 nanometers, respectively. Although a combination of other conductive materials can be included in the layer 658, such as platinum, titanium, chromium, palladium, gold, silver, combinations of these, etc. The conductive layer 658 is disposed over the sidewalls of the trench to form the two facing electrodes 610, 612. In addition, the conductive layer 658 forms the conductive mounting pads 620, 622 in the region of the top surface of the substrate 630 not coated by the negative photoresist 654.

As shown in FIG. 6L, sputtered conductive material may also be formed along the bottom of the cavities, as illustrated by the material 662 formed on the bottom of the cavity 656a. However, the shape of the isotropically etched cavities 656a-c, which have widths greater than the width of their respective trenches helps ensure that at least a portion of the cavities are not coated by the conductive layer 658, and the interruption in the conductive layer 658 electrically separates the conductive electrodes 610, 612 on the sidewalls of the trench 632. For example, the top edge 660 of the cavity 656c, which does not have a line-of-sight through any of the trenches, is not coated by the conductive material 658. As a result, the conductive layers formed along the sidewalls of the respective trenches (i.e., the electrodes 610, 612) are not electrically connected to one another across the bottom of the trench 632.

FIG. 6L also illustrates the junctions 664a-b between cavities formed in adjacent trenches as a result of the isotropic etching procedure described in connection with FIG. 6K. For example, the cavity 656b that originates from the trench 632 expands to join with the cavity 656c that originates from the trench 634c, at cavity junction 664b.

Figure 6M:
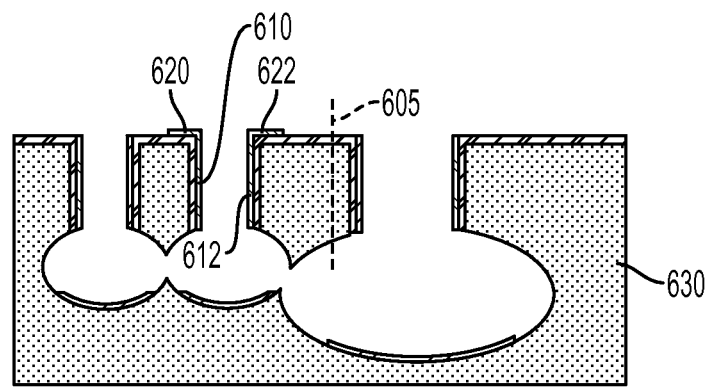

FIG. 6M illustrates lifting off the negative photoresist 654, which exposes the portions previously covered by the negative photoresist 654. Following lift off, the fabricated structure includes electrically disconnected facing electrodes 610, 612 situated on opposing sidewalls of the trench 632, and the connection pads 620, 622 connected to each of the electrodes 610, 612. The sensor 600 is then diced along line 605 to separate the sensor 600 from the working substrate 630. As can be appreciated from FIG. 6M, the adjacent trench 634c, and the cavity 656c formed at the base thereof, allows the sensor 600 to be diced and removed.

Figure 6N:
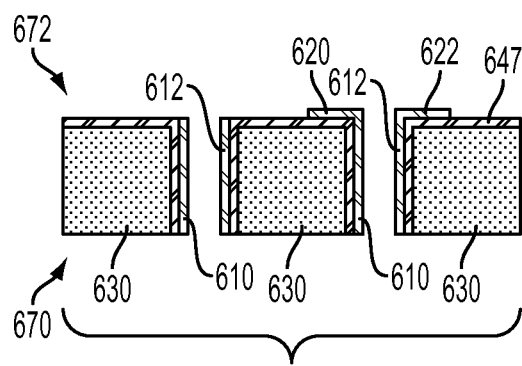

FIG. 6N illustrates the diced sensor 600 after mechanical polishing. In particular, the side of the working substrate 630 formed by the overlapping cavities expanding from the bases of the trench 632 may have a rough and/or uneven surface. That surface may then be polished by a mechanical process (without interfering with the electrodes 610, 612) to create a smooth bottom surface 670 for the sensor 600. The bottom surface 670 can be on an opposite side of the sensor from the mounting surface 672. When the completed sensor 600 is mounted over a substrate, the mounting surface 672 can be against the substrate and the smooth bottom surface 670 can be positioned to face outward, away from the substrate.

Once completed, the sensor 600 may be incorporated in a body-mountable device. For example, the sensor 600 could be incorporated in an eye-mountable device similar to the eye-mountable devices 110, 210 described above by flip-chip mounting the conductive terminals 620, 622 to corresponding pads on a substrate embedded in such a device. A controller connected to the pads can the operate the sensor 600 by applying an AC voltage to the electrodes 610, 612, measuring a current flowing through the sample volume formed by the trench 632, and using an antenna to wirelessly indicate the current measurement.

Figure 7:
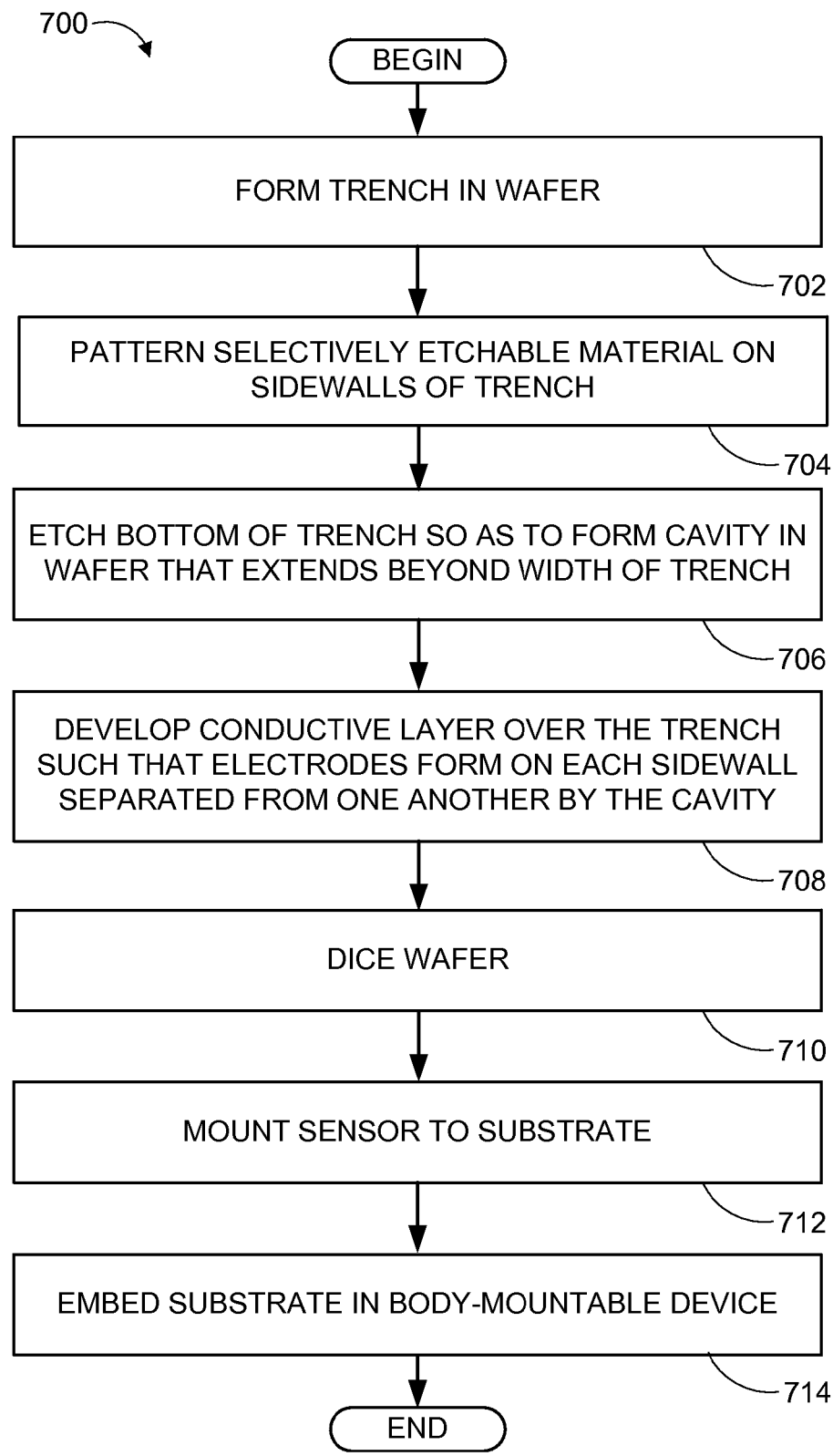
FIG. 7 is a flowchart of an example process for fabricating a conductivity sensor.

FIG. 7 is a flowchart of an example process 700 for producing a conductivity sensor. At block 702, a trench is formed in a wafer. For example, a combination of selectively etchable materials and/or photoresists can be patterned to selectively expose areas at which to form a trench, and deep reactive ion etching can be used to etch a trench into a silicon wafer. At block 704, a selectively etchable material is patterned on sidewalls of the trench. For example, a selectively etchable material (e.g., $SiO_2$) may be patterned over the trench structure and the base of the trench can be exposed via anisotropic reactive ion etching, leaving the selectively etchable material on the sidewalls. At block 706, the bottom of the trench can be etched with an isotropic etchant to form a cavity in the wafer that extends beyond the width of the trench. In some cases, cavities formed from the bases of adjacent trenches made in the substrate may expand into one another so as to join together. At block 708, a conductive layer can be developed over the trench such that electrodes form on each sidewall of the trench, and the electrodes are electrically separated from one another across the bottom of the trench by the cavity. For example, a conductive layer can be sputtered over the trench, and portions of the structure without line-of-sight to the sputtering source may remain uncoated by the conductive layer. At block 710, the wafer can be diced, which separates the conductivity sensor from the wafer. At block 712, the conductivity sensor can be mounted to a substrate. For example, the conductivity sensor can be flip-chip mounted to conductive pads on a substrate that also includes a controller and antenna, similar to the ophthalmic and/or body-mountable sensor platforms described in connection with FIGS. 1-3, for example. At block 714, the substrate can be mounted in an eye-mountable (or body-mountable) device. For example, the substrate may be encapsulated, partially or entirely, by polymeric material configured to mount to a body surface.

V. Additional Embodiments

It is particularly noted that while the electronics platform is described herein by way of example as an eye-mountable device or an ophthalmic device, it is noted that the disclosed systems and techniques for configurations of conductivity sensors can be applied in other contexts as well. For example, contexts in which fluid conductivity is measured in-vivo and/or from relatively small sample volumes, or are constrained to small form factors (e.g., implantable biosensors or other electronics platforms) may employ the systems and processes described herein. In one example, an implantable medical device that includes a conductivity sensor may be encapsulated in biocompatible material and implanted within a host. The implantable medical device may include a circuit configured to output an indication of a conductivity measurement (e.g., current reading). Reading and/or control devices can communicate with the implantable medical device to determine the current measurements.

For example, in some embodiments, the electronics platform may include a body-mountable device, such as a tooth-mountable device. In some embodiments, the tooth-mountable device may take the form of or be similar in form to the eye-mountable device 110, the eye-mountable device 210, and/or the body-mountable device 310. For instance, the tooth-mountable device may include a biocompatible polymeric material or a transparent polymer that is the same or similar to any of the polymeric materials or transparent polymers described herein and a substrate or a structure that is the same or similar to any of the substrates or structures described herein. In such an arrangement, the tooth-mountable device may be configured to measure conductivity of a fluid (e.g., saliva) of a user wearing the tooth-mountable device.

Moreover, in some embodiments, a body-mountable device may comprise a skin-mountable device. In some embodiments, the skin-mountable device may take the form of or be similar in form to the eye-mountable device 110, the eye-mountable device 210, and/or the body-mountable device 310. For instance, the skin-mountable device may include a biocompatible polymeric material or a transparent polymer that is the same or similar to any of the polymeric materials or transparent polymers described herein and a substrate or a structure that is the same or similar to any of the substrates or structures described herein. In such an arrangement, the body-mountable device may be configured to measure conductivity of a fluid (e.g., perspiration, blood, etc.) of a user wearing the body-mountable device.

Figure 8:
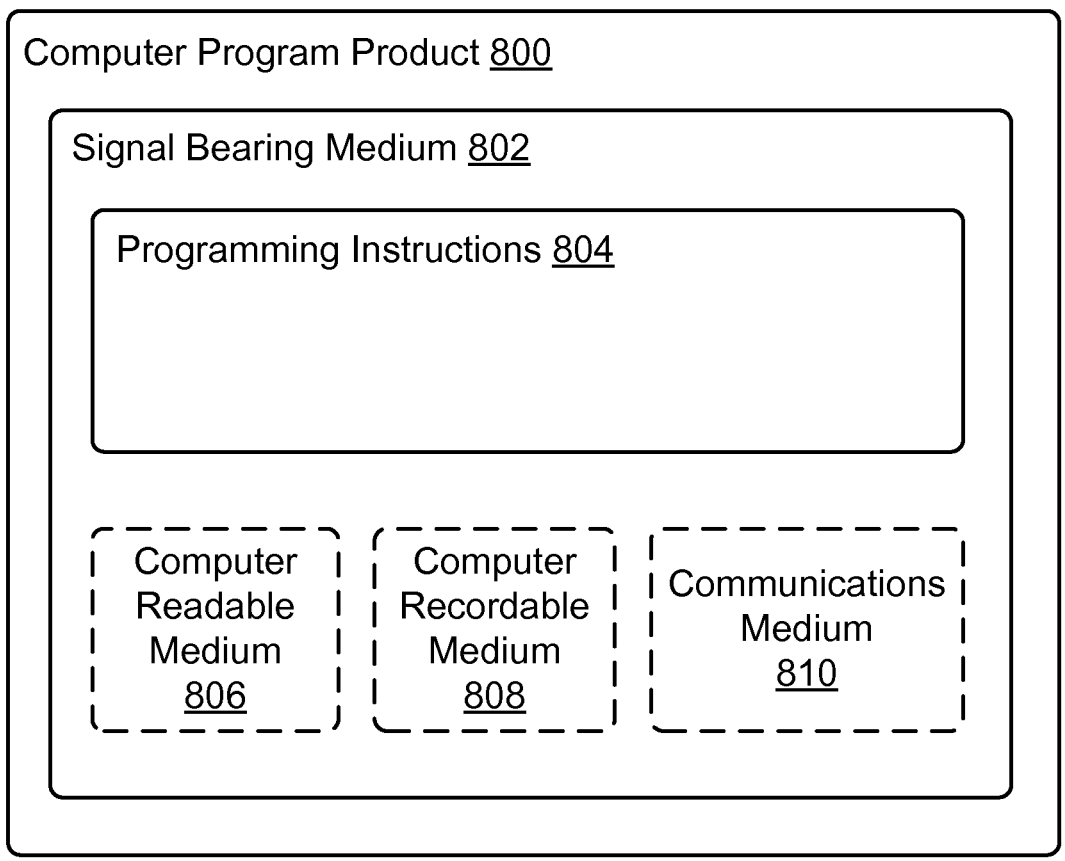
FIG. 8 depicts a computer-readable medium configured according to an example embodiment.

FIG. 8 depicts a computer-readable medium configured according to an example embodiment. In example embodiments, the example system can include one or more processors, one or more forms of memory, one or more input devices/interfaces, one or more output devices/interfaces, and machine-readable instructions that when executed by the one or more processors cause the system to carry out the various functions, tasks, capabilities, etc., described above.

As noted above, in some embodiments, the disclosed techniques can be implemented by computer program instructions encoded on a non-transitory computer-readable storage media in a machine-readable format, or on other non-transitory media or articles of manufacture. FIG. 8 is a schematic illustrating a conceptual partial view of an example computer program product that includes a computer program for executing a computer process on a computing device, arranged according to at least some embodiments presented herein, including the processes shown and described in connection with FIGS. 4A-4B and 7.

In one embodiment, the example computer program product 800 is provided using a signal bearing medium 802. The signal bearing medium 802 may include one or more programming instructions 804 that, when executed by one or more processors may provide functionality or portions of the functionality described above with respect to FIGS. 1-7. In some examples, the signal bearing medium 802 can include a non-transitory computer-readable medium 806, such as, but not limited to, a hard disk drive, a Compact Disc (CD), a Digital Video Disk (DVD), a digital tape, memory, etc. In some implementations, the signal bearing medium 802 can be a computer recordable medium 808, such as, but not limited to, memory, read/write (R/W) CDs, R/W DVDs, etc. In some implementations, the signal bearing medium 802 can be a communications medium 810, such as, but not limited to, a digital and/or an analog communication medium (e.g., a fiber optic cable, a waveguide, a wired communications link, a wireless communication link, etc.). Thus, for example, the signal bearing medium 802 can be conveyed by a wireless form of the communications medium 810.

The one or more programming instructions 804 can be, for example, computer executable and/or logic implemented instructions. In some examples, a computing device is configured to provide various operations, functions, or actions in response to the programming instructions 804 conveyed to the computing device by one or more of the computer readable medium 806, the computer recordable medium 808, and/or the communications medium 810.

The non-transitory computer readable medium 806 can also be distributed among multiple data storage elements, which could be remotely located from each other. The computing device that executes some or all of the stored instructions can be a microfabrication controller, or another computing platform. Alternatively, the computing device that executes some or all of the stored instructions could be remotely located computer system, such as a server.

While various aspects and embodiments have been disclosed herein, other aspects and embodiments will be apparent to those skilled in the art. The various aspects and embodiments disclosed herein are for purposes of illustration and are not intended to be limiting, with the true scope being indicated by the following claims.

What is claimed is:

1. An eye-mountable device comprising:
   a transparent polymeric material;
   a substrate at least partially embedded within the polymeric material;
   an antenna disposed on the substrate;
   a conductivity sensor disposed on the substrate, wherein the conductivity sensor includes:
   a frame having a trench formed therein that defines a fluid sample cell, wherein the trench includes a first sidewall and a second sidewall,
   a first electrode formed on the first sidewall, and
   a second electrode formed on the second sidewall such that the first and second electrodes are on opposite sides of the fluid sample cell; and
   a controller electrically connected to the sensor electrodes and the antenna, wherein the controller is configured to: (i) apply a voltage to the electrodes sufficient to generate a current through the electrodes related to a conductance of a fluid occupying the fluid sample cell; (ii) measure the generated current; and (iii) use the antenna to indicate the measured current.

2. The eye-mountable device of claim 1, wherein the first electrode and the second electrode are separated by a substantially constant separation distance throughout the fluid sample cell.

3. The eye-mountable device of claim 2, wherein the separation distance between the two electrodes is less than about 100 micrometers.

4. The eye-mountable device of claim 1, wherein the transparent polymeric material has a concave surface and a convex surface, and wherein the concave surface is configured to be removably mounted over a corneal surface and the convex surface is configured to be compatible with eyelid motion when the concave surface is so mounted.

5. The eye-mountable device of claim 4,
   wherein the first and second electrodes each include a width dimension and a length dimension;
   wherein the width dimension of each electrode extends along a depth of the fluid sample cell, which depth is oriented approximately perpendicular to a locally proximate region of the convex surface of the polymeric material; and
   wherein the length dimension of each electrode extends within a plane approximately co-planar with the locally proximate region of the convex surface.

6. The eye-mountable device of claim 4,
   wherein the two electrodes each substantially span a depth of the fluid sample cell that extends transverse to a locally proximate region of the convex surface of the polymeric material; and
   wherein the depth of the fluid sample cell is greater than about 20 micrometers.

7. The eye-mountable device of claim 6, wherein the depth of the fluid sample cell is between about 50 micrometers and about 100 micrometers.

8. The eye-mountable device of claim 4, wherein the polymeric material includes a channel situated so as to expose the electrodes to tear fluid, via the channel, when the concave surface is mounted over an eye.

9. The eye-mountable device of claim 4, wherein the polymeric material includes an electrolyte-absorbant silicon hydrogel in the vicinity of the electrodes so as to expose the electrodes to electrolytes in tear fluid, via diffusion through the silicon hydrogel, when the concave surface is mounted over an eye.

10. The eye-mountable device of claim 1, wherein the fluid sample cell has a volume less than about 100 nano liters.

11. The eye-mountable device of claim 1, wherein the voltage applied to the sensor electrodes is a periodically varying AC voltage which causes the generated current to be an AC current, and wherein the controller is further configured to generate the AC voltage and to measure the AC current.

12. The eye-mountable device of claim 1, wherein the frame of the conductivity sensor includes a silicon wafer.

13. The eye-mountable device of claim 1, wherein the transparent polymeric material includes a silicone elastomer.

14. The eye-mountable device of claim 1, further comprising an energy harvesting system that captures electrical energy from incident radiation to power the controller.

* * * * *